United States Patent
Leban et al.

(10) Patent No.: US 10,221,147 B2
(45) Date of Patent: Mar. 5, 2019

(54) HETEROCYCLIC COMPOUNDS WITH WORKING MEMORY ENHANCING ACTIVITY

(71) Applicant: Red Bull GmbH, Fuschl am See (AT)

(72) Inventors: Johann Leban, Vienna (AT); Gert Lubec, Vienna (AT)

(73) Assignee: Red Bull GmbH, Fuschl am See (AT)

( * ) Notice: Subject to any disclaimer, the term of this patent is extended or adjusted under 35 U.S.C. 154(b) by 0 days.

(21) Appl. No.: 15/429,961

(22) Filed: Feb. 10, 2017

(65) Prior Publication Data

US 2017/0174642 A1 Jun. 22, 2017

Related U.S. Application Data

(63) Continuation-in-part of application No. PCT/EP2015/068703, filed on Aug. 13, 2015.

(30) Foreign Application Priority Data

Aug. 13, 2014 (EP) ..................................... 14180847
Dec. 5, 2014 (EP) ..................................... 14196657

(51) Int. Cl.
*C07D 277/20* (2006.01)
*C07D 277/26* (2006.01)
(Continued)

(52) U.S. Cl.
CPC .......... *C07D 277/26* (2013.01); *A61K 9/4808* (2013.01); *A61K 31/426* (2013.01); *A61K 45/06* (2013.01)

(58) Field of Classification Search
CPC ... A61K 31/055; A61K 31/333; C07D 277/26
(Continued)

(56) References Cited

U.S. PATENT DOCUMENTS 7,297,817 B2 11/2007 Lesur et al.
7,449,481 B2 11/2008 Bacon et al.
(Continued)

FOREIGN PATENT DOCUMENTS

CN 17221400 A 1/2006
CN 1986527 A 6/2007
(Continued)

OTHER PUBLICATIONS

Cao J. et al. "*SARs at the Monoamine Transporters for a Novel Series of Modafinil Analogues*" ACS Med. Chem. Lett., 2(1) pp. 48-52, 2001.
(Continued)

*Primary Examiner* — Shengjun Wang
(74) *Attorney, Agent, or Firm* — Seed IP Law Group LLP

(57) ABSTRACT

The present disclosure relates to a chemical compound having the general formula formula (I)

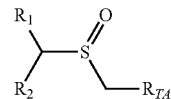

wherein $R_1$ and $R_2$ are, equal or independently, aryl, heteroaryl; wherein $R_{TA}$ is a 2-1,3-, or 4-1,3- or 5-1,3-thiazole ring and its use in for improving the short term memory and/or the working memory.

14 Claims, 7 Drawing Sheets

(51) Int. Cl.
  *A61K 9/48* (2006.01)
  *A61K 31/426* (2006.01)
  *A61K 45/06* (2006.01)

(58) Field of Classification Search
  USPC .......................................... 548/202; 514/365
  See application file for complete search history.

(56) References Cited

U.S. PATENT DOCUMENTS

2002/0183334 A1   12/2002   Bacon et al.
2005/0234040 A1   10/2005   Bacon et al.

FOREIGN PATENT DOCUMENTS

| EP | 1260501 A1 | 11/2002 |
| WO | 2003/059873 A1 | 7/2003 |
| WO | 2003/066035 A2 | 8/2003 |
| WO | 2005/028428 A1 | 3/2005 |
| WO | 2005/042479 A1 | 5/2005 |

OTHER PUBLICATIONS

Jung J. et al. "*Simple Synthesis of Modafinil Derivatives and Their Anti-Inflammatory Activity*" Molecules 17, 10446-10458, 2012.
Prisinzano T. et al. "*Synthesis and determination of the absolute configuration of the enantiomers of modafinil*", Tetrahedron:Asymmetry 15 pp. 1053-1058, 2004.

HETEROCYCLIC COMPOUNDS WITH WORKING MEMORY ENHANCING ACTIVITY

CROSS-REFERENCE TO RELATED APPLICATIONS

This application is a Continuation-in-Part application of International Patent Application No. PCT/EP2015/068703, filed Aug. 13, 2015, which claims priority to European Patent Application Nos. 14180847.7 and 14196657.2, filed Aug. 13, 2014 and Dec. 5, 2014, respectively, which applications are incorporated herein by reference in their entireties.

DESCRIPTION

Technical Field

The present disclosure provides novel compounds that can be used to improve cognitive functions such as short term memory and/or working memory in human individuals, in particular in aging individuals. The present disclosure also provides new compounds which can improve working memory performance.

Background

Working memory is the system that actively holds multiple pieces of transitory information in the mind, where they can be manipulated in a way that makes them useful for goal directed behavior. This involves execution of verbal and nonverbal tasks, such as reasoning and comprehension and makes them available for further information-processing (Becker J T et al. 1999 Brain Cogn 41 (1): 1-8). That is, it is considered that the working memory includes subsystems that store and manipulate visual images or verbal information, resp., and also a central executive that coordinates these subsystems. It has been proposed to include visual representation of the possible moves, and awareness of the flow of information into and out of memory, all stored for a limited amount of time (Schacter, Daniel (2009, 2011), Psychology Second Edition, United States of America, Worth Publishers, p. 227). The concept of a working memory is generally based on the Baddeley's model as proposed in 1974 and supplemented in 2000 (Baddeley, Alan D.; Hitch, Graham (1974). "Working Memory"., in Gordon H. Bower: "The psychology of learning and motivation 2", Academic Press, pages 47 to 89; Baddeley A. November 2000, "The episodic buffer: a new component of working memory?", Trends Cogn. Sci. (Regul. Ed.) 4 (11), pages 417 to 423). Working memory tasks are considered to require monitoring (i.e., manipulation of information or behaviors) as part of completing goal-directed actions in the setting of interfering processes and distractions. The cognitive processes needed to achieve this include the executive and attention control of short-term memory, which permit interim integration, processing, disposal, and retrieval of information. These processes have been found to be sensitive to age.

It is also well accepted that short-term memory is the capacity for holding a small amount of information in mind in an active, readily available state for a short period of time. The duration of short-term memory is believed to be in the order of seconds. A commonly cited capacity is 7±2 elements which can be simultaneously kept in the short-term memory (Miller G., March 1956, "The magical number seven plus or minus two: some limits on our capacity for processing information", Psychological Review 63 (2): 81-979). In contrast, long-term memory can hold an indefinite amount of information.

Working memory is mandatory for everyday life and is reduced in aging (Gazzaley A. et al. Nature Neuroscience 8, 1298-1300 (2000)). Apart from aging working memory deficits can be caused by underlying dementias which are commonly ascribed to central executive impairment and assumed to relate to frontal lobe dysfunction. Working memory is reduced in Parkinson's disease.

Patients suffering from dementia of the Alzheimer type (AD) are particularly impaired in the functioning of the central executive component of working memory. Performance failures on standard tests of attention and executive function reinforce this interpretation. Alzheimer's disease (AD) is the leading cause of dementia, there are 35 million people suffering from this progressive neurodegenerative disorder today. The number of patients with dementias will double by 2030 and it is estimated that more than 115 million people with brain disorder by 2050 will be affected. According to the Alzheimer's Association, AD is the third most expensive disease ranking after cardiovascular diseases and cancer. There is no cure and early preclinical diagnostic assay available for AD. Currently there is only symptomatic therapy available, which is not able to stop progression of the disease. Global costs of dementia (social care and medical costs) are currently more than 1% GDP and are likely to increase 85% by 2030. Donepezil, rivastigmine and galantamine—are known as cholinesterase inhibitors. Cholinesterase inhibitors, particularly rivastigmine and donepezil, may reduce the severity of some behavioral and psychological symptoms in dementia and help delay their onset of dementia. Cholinesterase inhibitors are especially effective in Lewy body dementia and dementia related to Parkinson's disease in treating agitation, apathy and psychotic symptoms. Memantine is a medium-affinity NMDA (N-methyl-D-aspartate) receptor antagonist. Memantine forms an independent class amongst modern anti-dementives due to its unique glutamatergic active principle, as a substance acting specifically on the glutamatergic neurotransmitter system, benzodiazepines, antidepressant, anticonvulsants and mood stabilizers. All aforementioned drugs can be used in combination.

It was also found that schizophrenics exhibit impaired spatial delayed-response tasks, in analogy to those that have been used to assess working memory function of the dorsolateral prefrontal cortex in rhesus monkeys. In this study schizophrenic patients and two control groups, normal subjects and bipolar psychiatric patients were tested on the oculomotor version of the memory task, a haptic version of the same task and two control tasks: i) a sensory task that did not require working memory and ii) a digit span test. Patients with schizophrenia showed marked deficits as compared to the two control groups (Sohee Park et al., Arch Gen Psychiatry, 1992, 49(12), 975 to 982). It was shown that spatial working memory in participants with childhood-onset schizophrenia and attention-deficit/hyperactivity disorder (ADHD) showed deficits in verbal and spatial working memory (Canan K. et al., Psychiatry Research, Volume 80, Issue 2, 17 Aug. 1998, pages 165 to 176).

Although numerous attempts have been made an efficient and effective way of how to cope with impairment of working memory or short term memory deficits has not been found yet.

In WO 03/059873 A1 pharmaceutical compounds are disclosed comprising both a thiazole group and a quaternary carbon comprising three phenyl groups next to a sulfoxide moiety. These compounds shall furnish a medicament which regulates calcium-activated potassium channels and which acts as modulator of SKca and/or IKca channels. According to this document the proposed pharmaceutical compounds shall be suited for the treatment of diseases or conditions like respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhea, ischemia, cerebral ischemia, ischemic hearth disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type 11, hyperinsulinemia, premature labor, baldness, cancer, and immune suppression in particular in for reducing or inhibiting undesired immune-regulatory actions, Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Crohn's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, auto-immune demyelinating diseases, Dupuytren's contracture, encephalomyelitis, encephalomyelitis allergic, endophthalmia phacoanaphylactica, enteritis allergic, auto-immune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to anti-spermatozoan antibodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Leishmania, and immunosuppressed disease states such as viral infections following allograft transplantations, graft vs. Host syndrome, transplant rejection, or AIDS, cancers, chronic active hepatitis diabetes, toxic chock syndrome, food poisoning, and transplant rejection.

US 2002/0183334 is about substituted thioacetamides. The rather broad set of compounds disclosed in US 2002/0183334 shall be suited for the treatment of sleepiness, tiredness, Parkinson's disease, cerebral ischemia, stroke, sleep apneas, eating disorders, attention deficit hyperactivity disorder, cognitive dysfunction, disorders associated with hypofunctionality of the cerebral cortex, depression, schizophrenia, and chronic fatigue syndrome, and also for the promotion of wakefulness, stimulation of appetite, or stimulation of weight gain.

In WO 03/066035 a broad range of thioether sulfonamides is disclosed which shall be suited for the treatment of diabetes mellitus.

US 2005/0234040 refers to tricyclic aromatic and bisphenyl sulfinyl derivatives. The compounds specified in this document shall furnish medicaments suited for the treatment of excessive sleepiness, promotion and/or improvement of wakefulness, preferably improvement of wakefulness in patients with excessive sleepiness associated with narcolepsy, sleep apnea, preferably obstructive sleep apnea/hypopnea, and shift work disorder), Parkinson's disease, Alzheimer's disease, cerebral ischemia, stroke, eating disorders, attention deficit disorder ("ADD"), attention deficit hyperactivity disorder ("ADHD"), depression, schizophrenia, fatigue, preferably fatigue associated with cancer or neurological diseases, such as multiple sclerosis and chronic fatigue syndrome, stimulation of appetite and weight gain and improvement of cognitive dysfunction.

Compounds and methods which are specifically designed for the improvement of short term and/or working memory are still missing.

SUMMARY AND INITIAL DESCRIPTION

Described herein are agents that increase short term memory and/or working memory performance, in some cases in both impaired as well as in healthy subjects. Also described herein are the treatment of age-dependent decline of working memory and/or short term memory and an effective agent which can be used for the treatment of disorders that in turn require improvement of working memory and/or short term memory.

The present disclosure provides a chemical compound having the general formula (I):

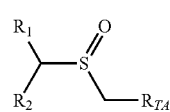

formula (I)

wherein $R_1$ and $R_2$ are, equal or independently, aryl, heteroaryl, fused aryl, fused heteroaryl, mono or multi-substituted aryl, mono or multi-substituted heteroaryl, mono or multi-substituted fused aryl, mono or multi-substituted fused heteroaryl;

$R_{TA}$ is a 2-1,3-, or 4-1,3- or 5-1,3-thiazole ring with the general Formula (IIa) or a 1,3,4-thiadiazole ring with the general Formula (IIb) or a 1,3,4-oxadiazole ring with the general Formula (IIc),

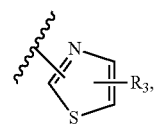

Formula (IIa)

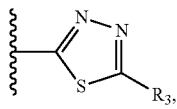

Formula (IIb)

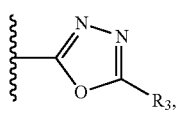

Formula (IIc)

R₃ is present 1 or 2 times, equal or independently, wherein R₃ is selected from the group consisting of hydrogen, alkyl, cycloalkyl, heterocycloalkyl, alkylamino, in some cases dialkylamino, arylamino, in some cases diarylamino, hydroxyalkylamino, alkoxy, arylalkyl, hydroxyalkyl, thioalkyl, haloalkyl, haloaryl, haloarylalkyl, haloalkoxy, mono or multi-substituted alkyl, mono or multi-substituted cycloalkyl, mono or multi-substituted heterocycloalkyl, mono or multi-substituted alkylamino, in some cases dialkylamino, mono or multi-substituted arylamino, in some cases diarylamino, mono or multi-substituted hydroxyalkylamino, mono or multi-substituted alkoxy, mono or multi-substituted arylalkyl, mono or multi-substituted hydroxyalkyl, mono or multi-substituted thioalkyl, mono or multi-substituted haloalkyl, mono or multi-substituted haloaryl, mono or multi-substituted haloarylalkyl, mono or multi-substituted haloalkoxy and carboxylate ester.

DETAILED DESCRIPTION

In one embodiment of the compound according to formula (I) substituted in the meaning of the present disclosure in some cases means substituted with a residue selected from the group consisting of alkyl, cykloalkyl, heterocycloalkyl, hydroxyalkyl, alkylthio, ether, hydroxyl, fluoride, chloride, bromide and iodide.

It has been found that those compounds according to formula (I) are rather pragmatic in which $R_3$ is hydrogen or alkyl, in some cases methyl, or hydroxyalkyl, in some cases hydroxymethyl. Those compounds according to formula (I) are also rather suited in which $R_3$ is alkyl substituted with at least one residue selected from the group consisting of heterocycloalkyl, carboxylic acid, amide and ester. Even more pragmatic in this regard are $R_3$ residues in which alkyl is methyl substituted with heterocycloalkyl, in some cases heterocycloalkyl containing at least two heteroatoms. That is, in this embodiment alkyl represents an alkylene bridging group, in some cases a methylene bridging group, between the heterocycle according to formula (IIa), (IIb) or (IIc) and the heterocycloalkyl group. Heterocycloalkyl is in some cases selected from the group consisting of morpholino, piperazino and methylpiperazino.

Aryl, i.e., an aryl group in the meaning of the present disclosure in some cases denotes phenyl, and substituted aryl in some cases denotes mono or multi-substituted phenyl. Exemplary substituted phenyl include for example $-o-C_6H_4-R'$, $-m-C_6H_4-R'$ and $-p-C_6H_4-R'$, wherein R' is an alkyl as defined herein or as defined for residues $R_3$, $R_4$, $R_5$, $R_6$ and $R_7$. Fused aryl in the meaning of the present disclosure in some cases denotes an aromatic ring being fused with at least one aromatic ring system, the fused aryl group in some cases being made of five to 15 carbon atoms, e.g., naphthyl and anthracenyl. These fused aryl may also be mono or multi-substituted, e.g., 1-naphthyl, 2-naphthyl, 1-anthracenyl or 2-anthracenyl, as defined herein.

Heteroaryl, i.e., a heteroaryl group in the meaning of the present disclosure in some cases denotes a 3 to 8-membered heterocyclic aromatic group which contains at least one heteroatom selected from the group consisting of O, N, and S. Heteroaryl in the meaning of the present disclosure also includes a heteroaryl ring being fused to another aromatic ring. Both heteroaryl and fused heteroaryl group can also be mono or multi-substituted as defined herein.

Alkyl, i.e., an alkyl group in the meaning of the present disclosure in some cases comprises an alkyl, alkenyl and alkynyl residue such as a $C_1$-$C_6$-alkyl, $C_2$-$C_6$-alkenyl and $C_2$-$C_6$-alkynyl residue. Suitable residues are selected from the group consisting of $-CH_3$, $-C_2H_5$, $-CH=CH_2$, $-C\equiv CH$, $-C_3H_7$, $-CH(CH_3)_2$, $-CH_2-CH=CH_2$, $-C(CH_3)=CH_2$, $-CH=CH-CH_3$, $-C\equiv C-CH_3$, $-CH_2-C\equiv CH$, $-C_4H_9$, $-CH_2-CH(CH_3)_2$, $-CH(CH_3)-C_2H_5$, $-C(CH_3)_3$, $-C_5H_{11}$, $-C_6H_{13}$, $-C(R')_3$, $-C_2(R')_5$, $-CH_2-C(R')_3$, $-C_3(R')_7$, $-C_2H_4-C(R')_3$, $-C_2H_4-CH=CH_2$, $-CH=CH-C_2H_5$, $-CH=C(CH_3)_2$, $-CH_2-CH=CH-CH_3$, $-CH=CH-CH=CH_2$, $-C_2H_4-C\equiv CH$, $-C\equiv C-C_2H_5$, $-CH_2-C\equiv C-CH_3$, $-C\equiv C-CH=CH_2$, $-CH=CH-C\equiv CH$, $-C\equiv C-C\equiv CH$, $-C_2H_4-CH(CH_3)_2$, $-CH(CH_3)-C_3H_7$, $-CH_2-CH(CH_3)-C_2H_5$, $-CH(CH_3)-CH(CH_3)_2$, $-C(CH_3)_2-C_2H_5$, $-CH_2-C(CH_3)_3$, $-C_3H_6-CH=CH_2$, $-CH=CH-C_3H_7$, $-C_2H_4-CH=CH-CH_3$, $-CH_2-CH=CH-C_2H_5$, $-CH_2-CH=CH-CH=CH_2$, $-CH=CH-CH=CH-CH_3$, $-CH=CH-CH_2-CH=CH_2$, $-C(CH_3)=CH-CH=CH_2$, $-CH=C(CH_3)-CH=CH_2$, $-CH=CH-C(CH_3)=CH_2$, $-CH_2-CH=C(CH_3)_2$, $-C(CH_3)=C(CH_3)_2$, $-C_3H_6-C\equiv CH$, $-C\equiv C-C_3H_7$, $-C_2H_4-C\equiv C-CH_3$, $-CH_2-C\equiv C-C_2H_5$, $-CH_2-C\equiv C-CH=CH_2$, $-CH_2-CH=CH-C\equiv CH$, $-CH_2-C\equiv C-C\equiv CH$, $-C\equiv C-CH=CH-CH_3$, $-CH=CH-C\equiv C-CH_3$, $-C\equiv C-C\equiv C-CH_3$, $-C\equiv C-CH_2-CH=CH_2$, $-CH=CH-CH_2-C\equiv CH$, $-C\equiv C-CH_2-C\equiv CH$, $-C(CH_3)=CH-CH=CH_2$, $-CH=C(CH_3)-CH=CH_2$, $-CH=CH-C(CH_3)=CH_2$, $-C(CH_3)=CH-C\equiv CH$, $-CH=C(CH_3)-C\equiv CH$, $-C\equiv C-C(CH_3)=CH_2$, $-C_3H_6-CH(CH_3)_2$, $-C_2H_4-CH(CH_3)-C_2H_5$, $-CH(CH_3)-C_4H_9$, $-CH_2-CH(CH_3)-C_3H_7$, $-CH(CH_3)-CH_2-CH(CH_3)_2$, $-CH(CH_3)-CH(CH_3)-C_2H_5$, $-CH_2-CH(CH_3)-CH(CH_3)_2$, $-CH_2-C(CH_3)_2-C_2H_5$, $-C(CH_3)_2-C_3H_7$, $-C(CH_3)_2-CH(CH_3)_2$, $-C_2H_4-C(CH_3)_3$, $-CH(CH_3)-C(CH_3)_3$, $-C_4H_8-CH=CH_2$, $-CH=CH-C_4H_9$, $-C_3H_6-CH=CH-CH_3$, $-CH_2-CH=CH-C_3H_7$, $-C_2H_4-CH=CH-C_2H_5$, $-CH_2-C(CH_3)=C(CH_3)_2$, $-C_2H_4-CH=C(CH_3)_2$, $-C_4H_8-C\equiv CH$, $-C\equiv C-C_4H_9$, $-C_3H_6-C\equiv C-CH_3$, $-CH_2-C\equiv C-C_3H_7$, and $-C_2H_4-C\equiv C-C_2H_5$;
wherein R' can be defined as residue $R_3$ as outlined above for formula (I). R' as referred to above in some cases is hydrogen, methyl, ethyl, n-propyl, i-propyl, n-butyl, tert-butyl, sec-butyl or isobutyl, and in some rather suitable cases hydrogen, methyl or i-propyl.

The alkyl group according to one embodiment of formula (I), in rather suitable cases for residue $R_3$, is methyl, ethyl, propyl, isopropyl, n-butyl, tert-butyl, sec-butyl, and isobutyl, in some cases methyl or isopropyl, and in some further cases alkyl is selected from the group consisting of methyl, ethyl, iso-propyl, and tert-butyl.

Arylalkyl, i.e., an arylalkyl group in the meaning of the present disclosure in some cases denotes a linear or branched $C_1$-$C_6$-alkyl substituted with at least one aryl group as defined above, such as benzyl or phenylethyl.

Suitable mono or multi-substituted arylalkyl comprise for example 4-hydroxybenzyl, 3-fluorobenzyl or 2-fluorophenylethyl.

Cycloalkyl, i.e., a cycloalkyl group in the meaning of the present disclosure in some cases denotes a non-aromatic ring system containing three to eight carbon atoms, such as four to eight carbon atoms. With mono or multi-substituted cycloalkyl one or more of the carbon atoms in the ring may be substituted by a group R' as defined above, in some cases methyl, ethyl, n-propyl, i-propyl, n-, i- or t-butyl. Suitable $C_3$-$C_8$-cycloalkyl groups can be selected from the group consisting of -cyclo-$C_3H_5$, -cyclo-$C_4H_7$, -cyclo-$C_5H_9$, -cyclo-$C_6H_{11}$, -cyclo-$C_7H_{13}$, and -cyclo-$C_8H_{15}$.

Heterocycloalkyl, i.e., heterocycloalkyl group in the meaning of the present disclosure in some cases denotes a non-aromatic carbon ring system in which one or more ring carbon atoms have been replaced by a heteroatom functional group such as O, S, SO, $SO_2$, N, or NR'2, wherein R' is defined as outlined above. Rather suited heterocycloalkyl groups can be selected from the group consisting of morpholine-4-yl, piperazinyl, and 1-alkylpiperazine-4-yl.

Hydroxyalkyl, i.e., a hydroxyalkyl group in the meaning of the present disclosure in some cases denotes a hydroxyalkyl group in which the alkyl group is defined as outlined above, such as methyl, ethyl, n-propyl, i-propyl, n-, i- or t-butyl. Suitable hydroxyalkyl groups are selected from the groups consisting of a hydroxymethyl, hydroxyethyl, hydroxypropyl, and hydroxy-iso-propyl group. The hydroxyalkyl group according to one embodiment of formula (I) is hydroxymethyl. Once bonded the alkyl or methyl group may also be denoted as alkylene or methylene group, respectively.

Alkylthio, i.e., an alkylthio group in the meaning of the present disclosure in some cases denotes an alkylthio group in which the alkyl group is defined as outlined above, such as for $R_3$, in some cases thiomethyl.

Haloalkyl, i.e., a haloalkyl group in the meaning of the present disclosure in some cases denotes a haloalkyl group in which the alkyl group is defined as outlined above, in rather suitable cases for $R_3$, and wherein said alkyl is substituted by one or more halogen atoms, such as substituted by one to five halogen atoms, in some cases by fluor or chlorine atoms. In one embodiment the haloalkyl group is selected from the group consisting of —$C(R^{10})_3$, —$CR^{10}(R^{10})_2$, —$CR^{10}(R^{10'})R^{10''}$, —$C_2(R^{10})_5$, —$CH_2$—$C(R^{10})_3$, —$C(R^{10})_2$—$CH(R^{10'})_2$, —$CH_2$—$CR^{10}(R^{10'})_2$, —$CH_2$—$CR^{10}(R^{10'})R^{10''}$, —$C_3(R^{10})_7$, or —$C_2H_4$—$C(R^{10})_3$, wherein $R^{10}$, $R^{10'}$, $R^{10''}$ represent F, Cl, Br or I, in some cases F.

Haloaryl, i.e., a haloaryl group in the meaning of the present disclosure in some cases denotes a haloaryl group in which at least one aromatic carbon atom is substituted by one or more halogen atoms, such as substituted by one to five halogen atoms. In some cases, halogen atoms are selected from the group consisting of fluorine, chlorine and bromine atoms, and such as fluorine.

Haloarylalkyl, i.e., a haloarylalkyl group in the meaning of the present disclosure in some cases denotes a haloarylalkyl group in which the arylalkyl group is defined as outlined above and wherein at least one aromatic carbon atom of said aryl group is substituted by one or more halogen atoms, such as substituted by one to five halogen atoms. In some cases, halogen atoms are selected from the group consisting of fluorine, chlorine, bromine and iodine atoms, in some further cases from fluorine and chlorine atoms.

Haloalkoxy, i.e., a haloalkoxy group in the meaning of the present disclosure in some cases denotes a haloalkoxy group in which the alkoxy group is defined as outlined above and wherein said alkoxy is substituted by one or more halogen atoms, such as substituted by one to five halogen atoms, in some cases by fluorine, chlorine, bromine and/or iodine atoms, in some other cases fluorine and/or chlorine atoms. In some cases, the haloalkoxy group is selected from the group consisting of —$OC(R^{10})_3$, —$OCR^{10}(R^{10'})_2$, —$OCR^{10}(R^{10'})R^{10''}$, —$OC_2(R^{10})_5$, —$OCH_2$—$C(R^{10})_3$, —$OCH_2$—$CR^{10}(R^{10'})_2$, —$OCH_2$—$CR^{10}(R^{10'})R^{10''}$, —$OC_3(R^{10})_7$ or —$OC_2H_4$—$C(R^{10})_3$, wherein $R^{10}$, $R^{10'}$, $R^{10''}$ represent F, Cl, Br or I, such as F.

Alkylamino, i.e., an alkylamino group in the meaning of the present disclosure in some cases denotes an alkylamino group in which the alkyl group is defined as outlined above, in rather suitable cases for $R_3$. The alkylamino group in the meaning of the present disclosure in some cases denotes a (alkyl)$_2$-N-group, i.e., a dialkylamino group, or a alkyl-NH— group. The dialkylamino group is used in some cases. Alkyl is in some cases defined as outlined above.

Arylamino, i.e., a diarylamino group in the meaning of the present disclosure in some cases denotes an arylamino group in which the aryl group is defined as outlined above. The arylamino group denotes a (aryl)$_2$-N-group, i.e., a diarylamino group, or a aryl-NH— group. The diarylamino group is used in some cases, in some other cases the diphenylamino group. Aryl is in some cases defined as outlined above.

Hydroxyalkylamino, i.e., an hydroxyalkylamino group in the meaning of the present disclosure in some cases denotes an hydroxyalkylamino group in which the alkyl group is defined as outlined above, in rather suitable cases for $R_3$, and wherein the hydroxyalkylamino group denotes a (HO-alkyl)$_2$-N-group or a HO-alkyl-NH— group, or a (HO-alkyl)-N-(alkyl)- group. Alkyl is in some cases defined as outlined above.

Those compounds according to formula (I) are rather pragmatic in which at least one of $R_1$ and $R_2$ is aryl or substituted aryl, in some cases phenyl or substituted phenyl, e.g., tolyl.

According to another embodiment of the compound of formula (I) $R_1$ is aryl or substituted aryl, in some cases phenyl or substituted phenyl, e.g., tolyl, and $R_2$ is heteroaryl or substituted heteroaryl.

According to an embodiment of the compound of formula (I) having a 1,3,4-oxadiazole ring with the formula (IIc) $R_3$ is hydrogen and $R_1$ and $R_2$ are aryl or substituted aryl, such as phenyl.

It has been found that most promising results can be obtained when in formula (I) both $R_1$ and $R_2$ are phenyl or substituted phenyl, such as phenyl. Moreover, those compounds according to formula (I) furnish particularly improved results in terms of cognitive functions such as short term memory and/or working memory, in some cases working memory, in which $R_{TA}$ is a thiazole group, such as a 2-thiazole group, especially 2-thiazole, or a 4-thiazole group, in some cases 2-methyl-4-thiazole. In another embodiment of the present disclosure $R_{TA}$ is a thiadiazole group, such as a 1,3,4-thiadiazole-5-oxyalkyl group, especially 1,3,4-thiadiazole-5-oxymethyl. And, in another embodiment of the compound according to formula (I) $R_{TA}$ is a 1,3,4-oxadiazole group, such as 1,3,4-oxadiazole.

Rather suitable compounds according to formula (I) in terms of improving cognitive functions, such as short term memory and/or working memory, in some cases working memory, are those selected from the group consisting of 2-(diphenylmethanesulfinylmethyl)-1,3-thiazole, 4-(diphenylmethanesulfinylmethyl)-1,3-thiazole, 2-(diphenylmethanesulfinylmethyl)-4-methyl-1,3-thiazole, 4-(diphenylmethanesulfinylmethyl)-2-methyl-1,3-thiazole, 2-(diphenylmethanesulfinylmethyl)-4-oxymethyl-1,3,4-thiadiazole, and 2-(diphenylmethanesulfinylmethyl)-1,3,4-oxadiazole, in some cases 4-(diphenylmethanesulfinylmethyl)-2-methyl-1,3-thiazole.

Rather pragmatic in this context, particularly with regard to working memory improvement, is 4-(diphenylmethanesulfinylmethyl)-2-methyl-1,3-thiazole.

Also rather suited are chemical compounds having the general formula (I), wherein $R_3$ is present on the thiazole ring $R_{TA}$ according to Formula (IIa) 2 times and independently selected from the group consisting of $R_4$, $R_5$, $R_6$ and $R_7$, wherein $R_1$ and $R_2$ are, equal or independently, aryl or substituted aryl, such as both are phenyl, wherein $R_{TA}$ is a 4-1,3-thiazole ring with the general Formula (IIIa)

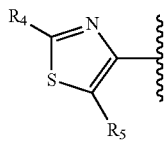

Formula (IIIa)

wherein $R_4$ is selected from the group consisting of oxirane, cyclopropyl, cyclobutyl, cyclopentyl and cyclohexyl, such as cyclopropyl, and wherein $R_5$ is selected from the group consisting of hydrogen, methyl, n-propyl, iso-propyl, such as hydrogen, or wherein $R_{TA}$ is a 5-1,3-thiazole ring with the general Formula (IIIb)

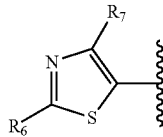

Formula (IIIb)

wherein $R_6$ is selected from the group consisting of hydrogen, methyl, n-propyl, iso-propyl, cyclopropyl, cyclobutyl, cyclopentyl and cyclohexyl, such as hydrogen, and wherein $R_7$ is selected from the group consisting of hydrogen, methyl, n-propyl, iso-propyl, fluoro, chloro, bromo, iodo, cyclopropyl, cyclobutyl, cyclopentyl and cyclohexyl, such as hydrogen.

The present disclosure further relates a chemical compound having the general formula (I):

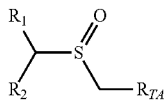

formula (I)

wherein $R_1$ and $R_2$ are, equal or independently, aryl or substituted aryl, in some cases both are phenyl, wherein $R_{TA}$ is a 4-1,3-thiazole ring with the general Formula (IIIa)

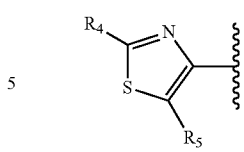

Formula (IIIa)

wherein $R_4$ is selected from the group consisting of oxirane, cyclopropyl, cyclobutyl, cyclopentyl and cyclohexyl, in some cases cyclopropyl, and wherein $R_5$ is selected from the group consisting of hydrogen, methyl, n-propyl, iso-propyl, fluoro, chloro, bromo and iodo, in some cases hydrogen, or wherein $R_{TA}$ is a 5-1,3-thiazole ring with the general Formula (IIIb)

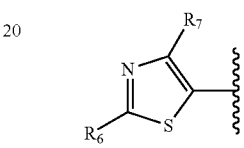

Formula (IIIb)

wherein $R_6$ is selected from the group consisting of hydrogen, methyl, n-propyl, iso-propyl, fluoro, chloro, bromo, iodo, cyclopropyl, cyclobutyl, cyclopentyl and cyclohexyl, in some cases hydrogen, and wherein $R_7$ is selected from the group consisting of hydrogen, methyl, n-propyl, iso-propyl, fluoro, chloro, bromo, iodo, cyclopropyl, cyclobutyl, cyclopentyl and cyclohexyl, such as hydrogen.

Those compounds according to formula (I) are rather suited in which at least one of $R_1$ and $R_2$ is aryl or substituted aryl, in some cases phenyl or substituted phenyl, e.g., tolyl. It has been found that most promising results can be obtained when in formula (I) both $R_1$ and $R_2$ are phenyl or substituted phenyl, such as phenyl.

In one embodiment of the compound according to formula (I) substituted in the meaning of the present disclosure in some cases means substituted with a residue selected from the group consisting of alkyl, cykloalkyl, heterocycloalkyl, hydroxyalkyl, alkylthio, ether, hydroxyl, fluoride, chloride, bromide and iodide. The alkyl group according to one embodiment of formula (I) is methyl, ethyl, propyl, isopropyl, n-butyl, tert-butyl, sec-butyl, and isobutyl, in some cases methyl or isopropyl, and in some further cases alkyl is selected from the group consisting of methyl, ethyl, isopropyl, and tert-butyl.

Those compounds according to formula (I) having residue (IIIa) are rather pragmatic in which $R_4$ is cyclopropyl and wherein $R_5$ is hydrogen.

Moreover, those compounds according to formula (I) having residue (IIIb) are rather suited in which both $R_6$ and $R_7$ are hydrogen.

And, those compounds according to formula (I) furnish particularly improved results in terms of cognitive functions such as short term memory and/or working memory, in some cases working memory, which are selected from the group consisting of 5-(diphenylmethanesulfinylmethyl)-1,3-thiazole, 5-(diphenylmethanesulfinylmethyl)-2-chloro-1,3-thiazole, 5-(diphenylmethanesulfinylmethyl)-2-methyl-1,3-thiazole, 5-(diphenylmethanesulfinylmethyl)-4-methyl-1,3-thiazole, 5-(diphenylmethanesulfinylmethyl)-4-chloro-1,3-thiazole, 5-(diphenylmethanesulfinylmethyl)-2-methyl-4-methyl-1,3-thiazole,
5-(diphenylmethanesulfinylmethyl)-2-methyl-4-chloro-1,3-thiazole,
5-(diphenylmethanesulfinylmethyl)-2-chloro-4-methyl-1,3-thiazole,
5-(diphenylmethanesulfinylmethyl)-2-cyclopropyl-1,3-thiazole,
4-(diphenylmethanesulfinylmethyl)-2-cyclopropyl-5-methyl-1,3-thiazole,
4-(diphenylmethanesulfinylmethyl)-2-cyclopropyl-5-chloro-1,3-thiazole,
4-(diphenylmethanesulfinylmethyl)-2-oxirane-1,3-thiazole, and
4-(diphenylmethanesulfinylmethyl)-2-cyclopropyl-1,3-thiazole.

Rather pragmatic compounds according to formula (I) in terms of improving cognitive functions, in some cases short term memory and/or working memory, such as working memory, are those selected from the group consisting of 4-(diphenylmethanesulfinylmethyl)-2-cyclopropyl-1,3-thiazole (compound (I) having residue (IIIa)) and 5-(diphenylmethanesulfinylmethyl)-1,3-thiazole (compound (I) having residue (IIIb)).

Accordingly, with the compounds according to formula (I), in some cases containing the group of the general formula (IIa) or (IIb), in some other cases (IIa), and in some further cases (IIIa) or (IIIb), and in even further cases 4-(diphenylmethanesulfinylmethyl)-2-cyclopropyl-1,3-thiazole and 5-(diphenylmethanesulfinylmethyl)-1,3-thiazole, a novel chemotype of compounds, in some cases with working memory enhancing effects, is provided with the present disclosure that can be used for improving cognitive functions, in some cases short term memory and/or working memory, in some other cases working memory, both with healthy, e.g., healthy aging, and impaired, e.g., impaired aging, individuals. Moreover, with the compounds of formula (I), in some cases 4-(diphenylmethanesulfinylmethyl)-2-cyclopropyl-1,3-thiazole and 5-(diphenylmethanesulfinylmethyl)-1,3-thiazole, also patients with dementing disorders where working memory and/or short term memory enhancing is of benefit can be effectively treated. That is, with the compounds of the present disclosure as specified with formula (I), in some cases containing the group of the general formula (IIa) or (IIb), in some other cases (IIa), and in some further cases (IIIa) or (IIIb), cognitive functions and in rather suitable cases the working memory in human individuals, in some rather pragmatic cases in aging individuals can be improved. Hence, the present disclosure provides a compound according to formula (I), in some cases 4-(diphenylmethanesulfinylmethyl)-2-cyclopropyl-1,3-thiazole and 5-(diphenylmethanesulfinylmethyl)-1,3-thiazole, for use in improving cognitive functions and in some cases the short term memory and/or working memory, in some rather suitable cases the working memory, in human individuals, in some rather pragmatic cases in aging individuals. However, in general with the present disclosure compounds of formula (I) as defined herein are provided for use in therapy, i.e., for use as a medicament.

It is of particular interest that with the compounds of formula (I), in some cases containing the group of the general formula (IIa) or (IIb), in some other cases (IIa), in some further cases (IIIa) or (IIIb), and in some rather suitable cases 4-(diphenylmethanesulfinylmethyl)-2-cyclopropyl-1,3-thiazole and 5-(diphenylmethanesulfinylmethyl)-1,3-thiazole, improvements in terms of cognitive functions, in some cases short term memory and/or working memory, can be accomplished with human individuals who do not have short term memory deficits and/or working memory deficits and/or cognitive defects. Accordingly, these results can be obtained with individuals who do not have short term memory deficits and/or working memory deficits and/or cognitive defects caused by diseases of the brain. The compounds according to the present disclosure can thus also be administered to and are also effective with healthy individuals to improve short term memory and/or working memory, in some cases working memory, and/or other cognitive abilities (or to overcome respective deficits). Accordingly, the present disclosure therefore also relates to the use of a compound according to the present disclosure for the improvement of short term memory and/or working memory, in some cases working memory, and/or cognitive deficits in healthy individuals, in some rather suitable cases in healthy aging individuals.

In addition, with the compounds of formula (I), in some cases containing the group of the general formula (IIa) or (IIb), in some other cases (IIa), in some further cases (IIIa) or (IIIb), and in some rather suitable cases 4-(diphenylmethanesulfinylmethyl)-2-cyclopropyl-1,3-thiazole and 5-(diphenylmethanesulfinylmethyl)-1,3-thiazole, improvements in terms of cognitive functions, in some cases short term memory and/or working memory, such as working memory, can also be accomplished with human individuals who have short term memory deficits and/or working memory deficits and/or cognitive defects, in some cases working memory deficits, caused by diseases of the brain. In this regard, a patient can be treated with the compounds according to formula (I), containing the group of the general formula (IIa) or (IIb), in some cases (IIa), in some other cases (IIIa) or (IIIb), and in some rather suitable cases 4-(diphenylmethanesulfinylmethyl)-2-cyclopropyl-1,3-thiazole and 5-(diphenylmethanesulfinylmethyl)-1,3-thiazole, who has short term memory deficits and/or working memory deficits and/or cognitive defects caused by Alzheimer; Down syndrome; vascular cognitive impairment; stroke; frontotemporal dementia; behavioral, semantic or progressive aphasia type dementia; dementia with Lewy bodies; subcortical dementias; Parkinson's disease dementia; alcohol related dementia; dementia caused by traumatic brain injury; Huntington's disease related dementia; AIDS-related dementia; attention deficit disorders; working memory deficiencies related to ageing; working memory disorders related to viral infections of the brain; or schizophrenia, or who has any form of cognitive impairment, in some cases working memory impairments.

The compounds according to formula (I) of the present disclosure, in some cases 4-(diphenylmethanesulfinylmethyl)-2-cyclopropyl-1,3-thiazole and 5-(diphenylmethanesulfinylmethyl)-1,3-thiazole, can be used alone or in combination with other cognitive enhancing compounds such as rivastigmine, donepezil, galanthamin, clozapine, risperidine, memantine, olanzapine, ariprazole, quitiapine, clozapine, D1 agonists, nicotinic alfa 7-agonists, d-serine, d-cycloserine. PDE2, 4,9 inhibitors, AMPA agonists, lamotrigine, n-desmethylclozapine, mGlu receptor agonists, GABA A receptor agonists, muscarinic 1 and 4 receptor agonists, to treat cognitive impairments and improve working memory and/or short term memory, in some cases working memory.

The compounds according to the present disclosure are particularly useful for treating patients having working memory deficits, short term memory deficits and/or cognitive defects due to particular demands in healthy and aging individuals, diseases of the brain, mental disorders or cognitive deficits, especially patients having Alzheimer, Down syndrome, stroke (vascular cognitive impairment), frontotemporal dementia, behavioral, semantic and progressive aphasia type dementia, dementia with Lewy bodies, subcortical dementias, and Parkinson's disease dementia, alcohol related dementia, dementia caused by traumatic brain injury, Huntington's disease related dementia, AIDS-related dementia, attention deficit disorders; working memory deficiencies related to ageing; working memory disorders related to viral infections of the brain; or schizophrenia.

The compound according to formula (I), in some cases containing the group of the general formula (IIa) or (IIb), in some other cases (IIIa) or (IIIb), and in some rather suitable cases 4-(diphenylmethanesulfinylmethyl)-2-cyclopropyl-1,3-thiazole and 5-(diphenylmethanesulfinylmethyl)-1,3-thiazole or (IIa), can be administered to a patient having or being at risk to develop any of the disorders referred to above in an effective amount. It is also possible to administer the compound to healthy individuals for improving working memory, short term memory and/or cognitive ability, in some cases for improving working memory.

According to a one embodiment, it is convenient to administer the compound according to the present disclosure, in some cases 4-(diphenylmethanesulfinylmethyl)-2-cyclopropyl-1,3-thiazole and 5-(diphenylmethanesulfinylmethyl)-1,3-thiazole, by a single dosage unit form, especially as a capsule or a tablet. A formulation of the present disclosure in some cases comprises a soft gelatine capsule containing at least one compound according to formula (I) dissolved in oil within the capsule with one or more emulsifying agents. Accordingly, gelatine capsules are rather suited which comprise one or more emulsifying agents and also at least one compound according to formula (I) dissolved in at least one oil.

Pragmatic dosages comprise administration dosages of about 1 mg/kg to about 10 mg/kg body weight. Suitable dosage forms also comprise formulations comprising at least one compound according to formula (I) in an amount of about 0.1 mg to about 10 g, in some cases of about 1 mg to about 1 g, and in some other cases of about 10 mg to about 200 mg.

According to one embodiment, the compound of formula (I) according to the present disclosure, in some cases 4-(diphenylmethanesulfinylmethyl)-2-cyclopropyl-1,3-thiazole and 5-(diphenylmethanesulfinylmethyl)-1,3-thiazole, can be part of formulations which contain at least or can be administered with one or more compounds, also referred to as co-agents, selected from the group consisting of Rivastigmine, Donepezil, Galanthamin, clozapine, risperidine, memantine, olanzapine, ariprazole, quitiapine, clozapine, D1 agonists, nicotinic alfa 7, agonists, d-serine, d-cycloserine, PDE2,4,9 inhibitors, AMPA agonists, Lamotrigine, n-desmethylclozapine, mGlu receptor agonists, GABA A receptor agonists, and Muscarinic 1 and 4 agonists or other potential cognitive enhancing compounds.

The present disclosure also provides the use of a compound according to formula (I), in some cases 4-(diphenylmethanesulfinylmethyl)-2-cyclopropyl-1,3-thiazole and 5-(diphenylmethanesulfinylmethyl)-1,3-thiazole, in the manufacture of a medicament for the improvement of cognitive functions in human individuals, in some cases for the improvement of the short term memory and/or of the working memory, in some cases working memory.

Moreover, the present disclosure also provides a pharmaceutical preparation, also referred to herein by pharmaceutical composition, comprising at least one compound according to formula (I), in some cases 4-(diphenylmethanesulfinylmethyl)-2-cyclopropyl-1,3-thiazole and 5-(diphenylmethanesulfinylmethyl)-1,3-thiazole, and at least one pharmaceutically acceptable carrier and/or diluent. Thus, according to another aspect, the present disclosure relates to a pharmaceutical preparation comprising a compound according to the present disclosure and a pharmaceutically acceptable carrier or diluent.

Pharmaceutical "carriers", "diluents" as well as "excipients" are substances to be admixed in a pharmaceutical composition as auxiliary substances to the compound according to the present disclosure or other compounds with pharmaceutical effect (e.g., that have also neurological or behavioral effects). These auxiliary substances do not have a pharmaceutical effect on their own (they are no "active substance" per se) but may assist to optimize the effectivity of the compound according to the present disclosure. The substances used as "carriers", "diluents" and "excipients" can often be used interchangeably (i.e., that substances that are used as "diluents" may also serve as "excipients" and/or "carriers").

In general, "carriers" are substances that improve the delivery and the effectiveness of drugs; "diluents" are substances that dilute the active substance in a pharmaceutical preparation; "excipients" are substances that are admixed to the pharmaceutical formulation for defining its releasing properties.

All such "carriers", "diluents" and "excipients" (i.e., auxiliary substances, sometimes also the term "excipient" is used as the general term including all such substances) are, as already stated, inactive substances formulated alongside the active ingredient ("API") of a medication, for the purpose of bulking-up formulations that contain potent active ingredients (thus often also referred to as "bulking agents", "fillers", or "diluents"). Bulking up allows convenient and accurate dispensation of a drug substance when producing a dosage form. They also can serve various therapeutic-enhancing purposes, such as facilitating drug absorption or solubility, or other pharmacokinetic considerations. Such substances can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients, carriers and diluents also depends upon the route of administration and the dosage form, as well as the active ingredient and other factors. Such substances e.g., serve as antiadherents, binders, coatings, disintegrants, fillers, flavors, colors, lubricants, glidants, sorbents, preservatives, sweeteners, etc.

Drug "carriers" are substances that serve as mechanisms to improve the delivery and the effectiveness of drugs. Drug carriers are usually used in sundry drug delivery systems such as: controlled-release technology to prolong in vivo drug actions; decrease drug metabolism, and reduce drug toxicity.

Carriers are generally also used in designs to increase the effectiveness of drug delivery to the target sites of pharmacological actions.

Drug "diluents" are usually substances that simply dilute or reconstitute a pharmaceutical composition (e.g., after storage in dry form).

The pharmaceutical composition with the at least one compound according to formula (I), in some cases 4-(diphenylmethanesulfinylmethyl)-2-cyclopropyl-1,3-thiazole and 5-(diphenylmethanesulfinylmethyl)-1,3-thiazole, usually comprises said compound in an amount of about 0.01 (% w/w) to about 80 (% w/w) in a solid composition or about 0.001 (% w/v) to about 80 (% w/v) in a liquid composition.

In some cases the compound according to the present disclosure is present in an amount of about 0.1 (% w/w) to about 50 (% w/w) in a solid composition or about 0.01 (% w/v) to about 10 (% w/v) in a liquid composition, especially of about 1 (% w/w) to about 0 (% w/w) in a solid composition or about 0.1 (% w/v) to about 5 (% w/v) in a liquid composition.

As already stated, in rather pragmatic cases, the compounds according to formula (I), in some cases 4-(diphenylmethanesulfinylmethyl)-2-cyclopropyl-1,3-thiazole and 5-(diphenylmethanesulfinylmethyl)-1,3-thiazole, are provided as a pharmaceutical composition, especially as a pharmaceutical single unit dosage form. Pharmaceutical compositions and single unit dosage forms provided herein comprise a prophylactically or therapeutically effective amount of one or more compounds according to formula (I) and optionally also one or more additional prophylactic or therapeutic agents (e.g., in some cases a compound provided herein, or other prophylactic or therapeutic agent), and one or more pharmaceutically acceptable carriers or excipients or diluents. In one embodiment of the present disclosure and in this context, the term "pharmaceutically acceptable" means approved by a regulatory agency of the Federal or a state government or listed in the European or U.S. Pharmacopeia or other generally recognized pharmacopeia for use in animals, and more particularly in humans.

The term "carrier" refers in one embodiment to a diluent, adjuvant (e.g., Freund's adjuvant (complete and incomplete)), or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions.

In one embodiment, pharmaceutical compositions and dosage forms comprise one or more excipients. Suitable excipients are well-known to those skilled in the art of pharmacy, and non-limiting examples of suitable excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form usually depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Examples of suitable excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatine, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants can be used in the compositions of the present disclosure to provide solid dosage forms such as tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Suitable disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Suitable lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The active ingredients described herein such as the compounds according to formula (I) and/or the co-agents provided herein can be administered by controlled release means or by delivery devices that are well known to those of ordinary skill in the art. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients. Thus provided are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are in certain embodiments sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

According to a one embodiment of the present disclosure, the pharmaceutical preparation of the present disclosure further comprises one or more compounds selected from the group consisting of Rivastigmine, Donepezil, Galanthamin, clozapine, risperidine, memantine, olanzapine, ariprazole, quitiapine, clozapine, D1 agonists, nicotinic alfa 7, agonists, d-serine, d-cycloserine, PDE2,4,9 inhibitors, AMPA agonists, Lamotrigine, n-desmethylclozapine, mGlu receptor agonists, GABA A receptor agonists, and Muscarinic 1 and 4 agonists or other potential cognitive enhancing compounds, agents.

Rather pragmatic dosages of the compound according to formula (I), in some cases 4-(diphenylmethanesulfinylmethyl)-2-cyclopropyl-1,3-thiazole and 5-(diphenylmethanesulfinylmethyl)-1,3-thiazole, are 0.1 mg to 10 g, in some other cases of 1 mg to 1 g, especially 10 mg to 200 mg, of the compound according to the present disclosure. As already stated, the present disclosure relates to the use of a composition according to formula (I) for the manufacture of a medicament. And, the present disclosure also relates to the use of a composition comprising at least one compound according to formula (I) for the manufacture of a remedy, i.e., pharmacological treatment or prevention of cognitive impairment, dementia and deficits of short term and/or working memory.

The compound of the formula (I), in some cases 4-(diphenylmethanesulfinylmethyl)-2-cyclopropyl-1,3-thiazole and 5-(diphenylmethanesulfinylmethyl)-1,3-thiazole, can be administered to humans, rodents other mammals, as therapeutics per se, and as mixtures with one another or in the form of pharmaceutical preparations which allow enteral or parenteral use and which as active constituent contain an effective dose of the compound of formula (I). The effective dose range can easily be adapted to the severity and the need of the individual patient. Pragmatic doses are from 1 mg to 10 mg/kg body weight, in addition to customary pharmaceutically innocuous excipients and additives.

The proposed therapeutics can be administered orally, e.g., in the form of pills, tablets, coated tablets, sugar coated tablets, hard and soft gelatin capsules, solutions, syrups, emulsions or suspensions. Administration, however, can also be carried out rectally, e.g., in the form of suppositories, or parenterally, e.g., in the form of injections or infusions or percutaneously, e.g., in the form of ointments, creams or tinctures.

In addition to the active compound of formula (I), the pharmaceutical composition can contain further customary, usually inert carrier materials or excipients, in some cases as outlined above. Thus, the pharmaceutical preparations can also contain additives, such as, for fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants.

The compounds of the present disclosure can be used in the form of one substance alone or in combination with other active compounds—for example with remedies already known to improve short term memory and/or working memory of healthy individuals, in some cases of healthy aging individuals, and in some cases the working memory.

The present disclosure also provides a pharmaceutical composition comprising compounds of formula (I), in some cases 4-(diphenylmethanesulfinylmethyl)-2-cyclopropyl-1, 3-thiazole and 5-(diphenylmethanesulfinylmethyl)-1,3-thiazole, in free form or in the form of pharmaceutically acceptable formulations and together with pharmaceutically acceptable diluents or carriers.

The compounds of formula (I), in some cases 4-(diphenylmethanesulfinylmethyl)-2-cyclopropyl-1,3-thiazole and 5-(diphenylmethanesulfinylmethyl)-1,3-thiazole, and also the pharmaceutically acceptable salt or solvate thereof can be used as the active principle for improvement of cognitive functions, in some cases for the enhancement of short term memory and/or working memory, also in healthy or unimpaired individuals.

The compound according to the present disclosure is defined by formula (I), wherein the connection between the methylene group and the heterocyclic compound $R_{T4}$ can be with any position where there is no $R_3$ and where there is a free valence available for the formation of a covalent bond. As well, the connection between $R_3$ with the heterocycle can be with any position where the connection of the methylene group is not present and where there is a free valence available for the formation of a covalent bond. $R_3$ is present in formulae (IIa), (IIb) and (IIc) independently 1, or 2 times, equal or independently. $R_3$ in some cases is hydrogen or an alkyl group, in some other cases methyl, ethyl, iso-propyl, tert-butyl, or a hydroxyalkyl group, in some cases hydroxymethyl, or a cycloalkyl group, or a heterocycloalkyl group, or a dialkylamino group, in some cases dimethylamino, or a heterocycloalkyl group, in some cases morpholino, piperazino or methylpiperazino.

Compounds having infinite chains consisting for instance of repeating $R_1$, $R_2$ $R_3$ units and the like are not encompassed by this invention.

Constituents which are optionally substituted as stated herein, may be substituted, unless otherwise noted, at any chemically possible position.

The present disclosure also provides a pharmaceutical composition comprising a compound of Formula (I), in some cases 4-(diphenylmethanesulfinylmethyl)-2-cyclopropyl-1,3-thiazole and 5-(diphenylmethanesulfinylmethyl)-1, 3-thiazole, in free form or in the form of pharmaceutically acceptable salts and/or physiologically functional derivatives, together with a pharmaceutically acceptable diluent or carrier therefore. The present disclosure also relates to a compound of Formula (I) and physiologically acceptable salts or physiologically functional derivatives thereof. The compounds of the present disclosure according to Formula (I), in some cases 4-(diphenylmethanesulfinylmethyl)-2-cyclopropyl-1,3-thiazole and 5-(diphenylmethanesulfinylmethyl)-1,3-thiazole), are many times more effective and also many times more selective than for example Modafinil (2-(diphenylmethyl) sulfinyl acetamide).

In addition, the present disclosure provides methods for preparing the desired compounds: Such a method uses procedures from different publications (Jae-Chul Jung et al. Molecules 2012, 17, 10446-10458; WO 2005028428 A1, Jianjing Cao, ACS Med Chem Lett. 2010 Oct. 10; 2(1): 48-52; U.S. Pat. No. 7,297,817 B2, U.S. Pat. No. 7,449,481 B2, U.S. Pat. No. 7,314,875 B2; Faming Zhuanli Shenqing Gongkai Shuomingshu, CN 2005-10049330 20050310, 2006; Prisinzano, T. et al., Tetrahedron Asymm. 2004, 15, 1053-1058; EP 1 260 501 A1, CN 2006/10155494 20061227, 2007; WO 2005/042479 A1. The compound according to formula (I) can be obtained by the methods described herein or variations thereof in the racemic form.

Several processes are available for the preparation of compounds of Formula (I). These methods comprise the step of reacting benzhydrole with thioacetic acid or in some cases of thioglycolic acid, converting the carboxylic acid into an amide then into a thionamide, then into a thiazole. The thiazole can be converted by oxidation into the racemic compound of the Formula (I).

Alternatively, it is also possible to start from benzhydrol, converting it to the thiol, reacting it with a chloromethyl-heterocycle and oxidizing it with hydrogenperoxide.

For example 2-(diphenylmethanesulfinylmethyl)-1,3-thiazole was synthesized by condensing benzhydrole and mercaptoacetic acid with trifluoroacetic acid (TFA). Converting the acid to the acid chloride with thionylchloride and to the amide with ammonia. The thiazole was formed with 1,2-dichloro-1-ethoxyethane and the resulting sulfide oxydize to the sulfone with hydrogenperoxide.

In another example, benzhydrol was converted to the thiol with Lawesson's reagent and then alkylated with a chloromethyl-heterocycle. The resulting sulfide was converted to the sulfoxyde with hydrogen peroxide.

Accordingly, the compounds of the present disclosure can be prepared by use of a process comprising reacting diarylmethanol, in some cases benzhydrol, with Lawesson's reagent, treating the reaction product diarylmethanethiol with a chloromethyl-thiazole, -thiadiazole or -oxadiazole derivative, in some cases with 2-(chloromethyl)-1,3-thiazole, 4-(chloromethyl)-1,3-thiazole, 2-(chloromethyl)-4-methyl-1,3-thiazole, 4-(chloromethyl)-2-methyl-1,3-thiazole, 2-(chloromethyl)-4-oxymethyl-1,3,4-thiadiazole, or 2-(chloromethyl)-1,3,4-oxadiazole, and oxidizing the ((diarylmethyl)sulfanyl)methyl-thiazole, -thiadiazole or -oxadiazole derivative to the corresponding diarylmethanesulfinylmethyl compound.

Alternatively, the compounds of the present disclosure can be prepared by a process comprising reacting diarylmethanol, in some cases benzhydrol, with thioglycolic acid to form 2-(diarylmethylthio) acetic acid, converting said acetic acid derivative to 2-(diarylmethylthio) acetamide, converting said acetamide derivative, in some cases by treatment with Lawesson's reagent, to the corresponding ethanethioamide derivative, converting said ethanethioamide derivative to a (((diarylmethyl)sulfanyl)methyl) thiazole derivative, in some cases to 2-(diphenylmethanesulfanylmethyl)-1,3-thiazole, 4-(diphenylmethanesulfanylmethyl)-1, 3-thiazole, 2-(diphenylmethanesulfanylmethyl)-4-methyl-1, 3-thiazole or 4-(diphenylmethanesulfanylmethyl)-2-methyl-1,3-thiazole, and oxidizing said thiazole compound to the corresponding (diarylmethanesulfinylmethyl) thiazole derivative.

The present disclosure also contemplates a pharmaceutical composition comprising a compound of the general Formula (I), in some cases 4-(diphenylmethanesulfinylmethyl)-2-cyclopropyl-1,3-thiazole and 5-(diphenylmethanesulfinylmethyl)-1,3-thiazole, in free form and also to the use of in free form and physiologically functional derivatives, together with pharmaceutically acceptable diluents or carriers.

The present disclosure also relates to the use of the compound of the Formula (I), in some cases 4-(diphenylmethanesulfinylmethyl)-2-cyclopropyl-1,3-thiazole and 5-(diphenylmethanesulfinylmethyl)-1,3-thiazole, and also to the use of physiologically functional derivatives in the manufacture of a medicament for the cognitive enhancement of healthy individuals or aging individuals or of individuals with cognitive impairments, or for the treatment of a disease or a therapeutic indication in which improvement of cognitive functions, in some cases of the working memory is beneficial.

In some rather suitable cases, the pharmaceutical composition according to the present disclosure comprises a compound as defined by Formula (I), in some cases 4-(diphenylmethanesulfinylmethyl)-2-cyclopropyl-1,3-thiazole and 5-(diphenylmethanesulfinylmethyl)-1,3-thiazole, in free form and a pharmaceutically acceptable diluent or carrier for use in the treatment of healthy individual or aging individuals or treatment of a disease or medical condition accompanied by working memory deficits.

However, in general with the present disclosure also a pharmaceutical composition has been provided comprising a compound according to formula (I) and at least one pharmaceutically acceptable carrier and/or diluent, as defined herein, for use in therapy, i.e., for use as a medicament.

The present disclosure also relates to a pharmaceutical composition comprising a compound as defined herein in free form or in the form of a pharmaceutically acceptable diluents or carrier for use in the treatment of healthy individuals or aging individuals or for the treatment of a disease or medical condition accompanied by working memory deficits.

Accordingly, the problem of the present disclosure is also solved by a compound according to Formula (I), in some cases 4-(diphenylmethanesulfinylmethyl)-2-cyclopropyl-1,3-thiazole and 5-(diphenylmethanesulfinylmethyl)-1,3-thiazole, for use in improving cognitive functions in human individuals, in some cases in aging individuals. In rather suitable cases, said compound for use is used in improving the short term memory and/or the working memory in human individuals, in some cases for use in improving the working memory. The compound can in some cases be used for improving cognitive functions, in some cases short term and/or working memory, with human individual who do not have defects of cognitive functions and/or short term memory deficits and/or working memory deficits, or any such defects or deficits caused by diseases of the brain. Alternatively, the compound according to Formula (I), in some cases 4-(diphenylmethanesulfinylmethyl)-2-cyclopropyl-1,3-thiazole and 5-(diphenylmethanesulfinylmethyl)-1,3-thiazole, can be used for human individuals who have defects of cognitive functions and/or short term memory deficits and/or working memory deficits caused by diseases of the brain. The causes for such defects of cognitive functions and/or short term memory deficits and/or working memory deficits are those as mentioned above.

Accordingly, the problem of the present disclosure is also solved by the use of a compound according to Formula (I) for the preparation of a medicament for improving cognitive functions in human individuals, in some cases in aging individuals. In some rather suitable cases, said prepared medicament is used in improving the short term memory and/or the working memory in human individuals, in some cases for use in improving the working memory. Said prepared medicament can in some cases be used for improving cognitive functions such as short term and/or working memory, with human individual who do not have defects of cognitive functions and/or short term memory deficits and/or working memory deficits, or any such defects or deficits caused by diseases of the brain. Alternatively, said medicament prepared by use of the compound according to Formula (I), in some cases 4-(diphenylmethanesulfinylmethyl)-2-cyclopropyl-1,3-thiazole and 5-(diphenylmethanesulfinylmethyl)-1,3-thiazole, can be used for treating human individuals who have defects of cognitive functions and/or short term memory deficits and/or working memory deficits caused by diseases of the brain. The causes for such defects of cognitive functions and/or short term memory deficits and/or working memory deficits are those as mentioned above.

It has also surprisingly been found that the compound according to Formula (I), such as 4-(diphenylmethanesulfinylmethyl)-2-cyclopropyl-1,3-thiazole and 5-(diphenylmethanesulfinylmethyl)-1,3-thiazole, can be used in specifically inhibiting the dopamine transporter (DAT) in mammals, such as human individuals, while the norepinephrine transporter (NET) and the serotonin transporter (SERT) are not or are not significantly inhibited. That is the compound according to Formula (I) has reduced or in some cases essentially no activity on norepinephrine transporter (NET) and on serotonin transporter (SERT). This is preferred as activity on NET and SERT can lead to unwanted side effects. Accordingly, the present disclosure also is about use of the compound according to Formula (I) for improving or treating a condition in human individuals susceptible to substantially selectively inhibiting the dopamine transporter (DAT), in some cases without having substantially any, or only having reduced, activity on norepinephrine transporter (NET) and/or on serotonin transporter (SERT). And, the present disclosure also is about use of the compound according to Formula (I), in some cases 4-(diphenylmethanesulfinylmethyl)-2-cyclopropyl-1,3-thiazole and 5-(diphenylmethanesulfinylmethyl)-1,3-thiazole, for the preparation of a medicament for improving or treating a condition in human individuals susceptible to substantially selectively inhibiting the dopamine transporter (DAT), preferably without having substantially any, or only having reduced, activity on norepinephrine transporter (NET) and/or on serotonin transporter (SERT).

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art and include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, /ert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Specifically suitable salt forms are hexaflorophosphate and chloride salts.

Such salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like. The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

The compounds according to the present disclosure may also be provided as solvates. "Solvate" refers to a compound provided herein or a salt thereof that further includes a stoichiometric or non-stoichiometric amount of solvent bound by non-covalent intermolecular forces. Where the solvent is water, the solvate is a hydrate.

DESCRIPTION OF THE DRAWINGS

The present disclosure is further described by the following examples given in figures, yet without being restricted thereto.

EXAMPLES

Figure 1:
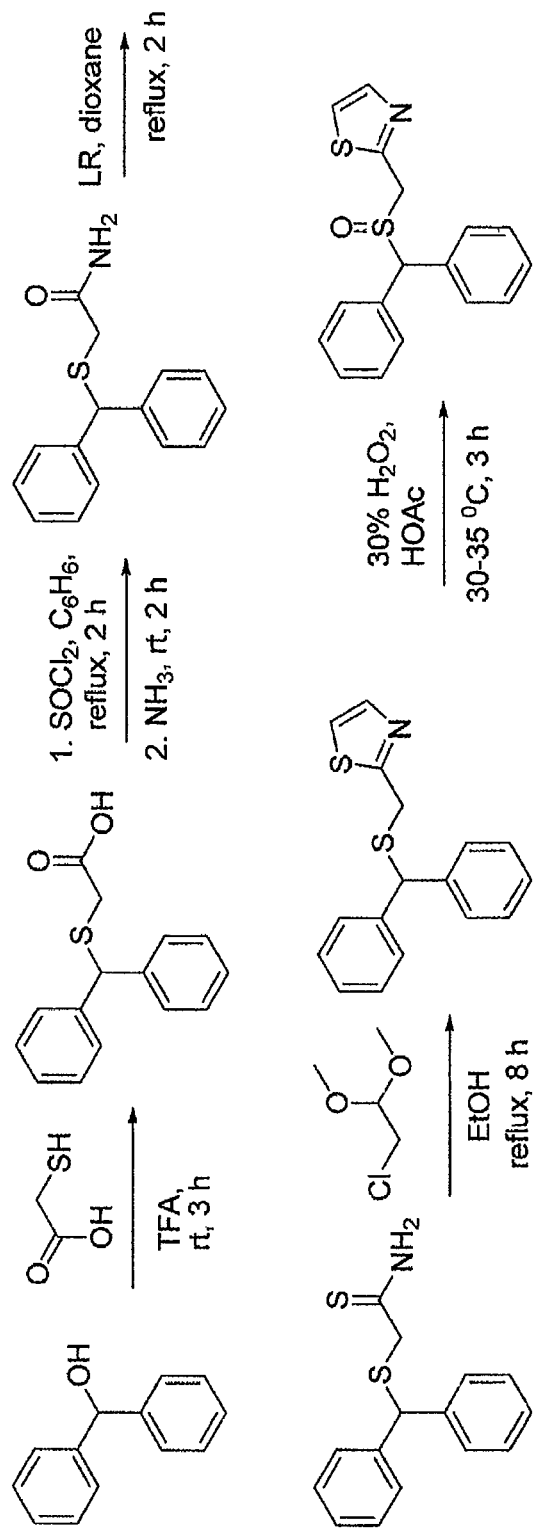
FIG. 1 shows scheme (1) for the synthesis of compounds as exemplified by 2-(diphenylmethanesulfinylmethyl}-1,3-thiazole (C1)

Materials:
The following compounds were purchased:
1. Diphenylmethane (Sigma Aldrich Chemie GmbH, Germany)
2. Thioglycolic acid (Sigma Aldrich Chemie GmbH, Germany)
3. Thionylchloride (Sigma Aldrich Chemie GmbH, Germany)
4. LR, Lawesson's Reagent (Sigma Aldrich Chemie GmbH, Germany)
5. Dioxane (Sigma Aldrich Chemie GmbH, Germany)
6. Trifluoroacetic acid (Sigma Aldrich Chemie GmbH, Germany)
7. Hydrogen peroxyde (Sigma Aldrich Chemie GmbH, Germany)
8. 1,2 dichloroethyl ether (ABCR GmbH & Co. KG, Germany)
9. 4-(chloromethyl)-1,3-thiazole (Sigma Aldrich Chemie GmbH, Germany)
10. Chloroacetaldehyde dimethyl acetal (MerckSchuchardt OHG, Germany)
11. Potassium tert-butoxide (Sigma Aldrich Chemie GmbH, Germany)
12. Solvents generally (Sigma Aldrich Chemie GmbH, Germany)

A. Syntheses

Analytics:
Abbreviations: min, minute(s); h, hour(s); r.t., room temperature; Rt, retention time; Ψ, pseudo; s, singlet; t, triplet, quint, quintet; br., broad; J, coupling constant; pTLC, preparative thin layer chromatography; DMAP, 4-dimethylaminopyridine.

Analytical TLC: Merck aluminum sheets, silica gel 60 F254.

Preparative TLC: Merck PLC plates, silica gel 60 F254, 0.5 mm, 1.0 mm or 2.0 mm.

Flash chromatography: Acros silica gel 60A, 0.035-0.070 mm. Flash Master Personal or Flash Master II, Jones Chromatography, UK.

NMR spectra: Bruker Avance 400 MHz. The $^1$H NMR spectra were recorded at 400 MHz; concentration, 1 to 5 mg/mL; temperature, 305 K. The residual solvent peaks were used as the internal standards (DMSO-$d_6$: δ H 2.49, $δ_C$ 39.5; CDCl$_3$: $δ_H$ 7.24, $δ_C$ 77.0; CD$_3$OD: $δ_H$ 3.30, $δ_C$ 49.0). Alternatively, TMS was used as a standard (indicated with TMS).

Analytical LC/ESI-MS: Waters 2700 Autosampler. 2× Waters 600 Multisolvent Delivery System, Waters 600 Controller. 50 L sample loop. Column, Chromolith Speed ROD RP18e (Merck, Darmstadt), 50×4.6 mm, with 2 μm prefilter (Merck). Eluent A, H$_2$O+0.1% HCO$_2$H; eluent B, MeCN. Gradient, 2% B to 100% B within 4 min, then isocratic for 0.90 min, then back to 2% B within 0.15 min, then isocratic for 0.50 min; flow, 3 mL/min. Waters LCZ single quadrupol mass spectrometer with electrospray source. MS method, MS8minPM-80-800-20V; positive/negative ion mode scanning, m/z 80-800 or 80-900 in 1 s; capillary, 3.5 kV; cone voltage, 20 V; multiplier voltage, 400 V; probe and desolvation gas temperature, 120° C. and 350° C., respectively. Waters 2487 Dual 280/254 nm Absorbance Detector, set to 254 nm. Software, Waters Masslynx V 4.0.

1. Synthesis of 4-(diphenylmethanesulfinylmethyl)-1,3-thiazole (C2)

Mercaptobenzhydryl

To a mixture of benzhydrol (2.0 g, 10.8 mmol) and Lawesson's reagent (3.7 g, 9.1 mmol) in anhydrous dioxane (50 mL) was refluxed for 3 h under argon. The solvent was evaporated till dryness. The resulting oil was dissolved in DCM and washed with water. The residue was purified by flash column chromatography (hexane) to give mercaptobenzhydryl 1.36 g, yield 62%.

4-{[(diphenylmethyl)sulfanyl]methyl}-1,3-thiazole

To a solution of thiol (2.3 g, 11.5 mmol) in DMF (10 mL) was added potassium t-BuOK (1.68 g) and 4-(chloromethyl)-1,3-thiazole (1.25 g, 9.3 mmol), and the reaction mixture was stirred at room temperature overnight. The next day saturated aqueous NH$_4$Cl was added and the reaction mixture was extracted with Et$_2$O. After removal of the solvent, the residue was purified by silica gel chromatography (hexane, hexane:CH$_2$Cl$_2$ 1:1) to afford 4-[(benzhydrylthio)methyl]-1,3-thiazole 5 (2 g, 59%).

4-(diphenylmethanesulfinylmethyl)-1,3-thiazole 27.6% $H_2O_2$ (0.74 mL) was added to the solution of thiazole 5 (0.0067 mol, 2.0 g) in glasial acetic acid (20 mL). The reaction mixture was stirred at room temperature during 24 h. The solvent was evaporated in vacuum till dryness. The residue was diluted with water, the precipitate was filtered off and purified by flash chromatography (hexane: $CH_2Cl_2$ 1:1) to yield 4-(diphenylmethanesulfinylmethyl)-1,3-thiazole, 1.87 g as white solid, yield 89%.

Figure 3:
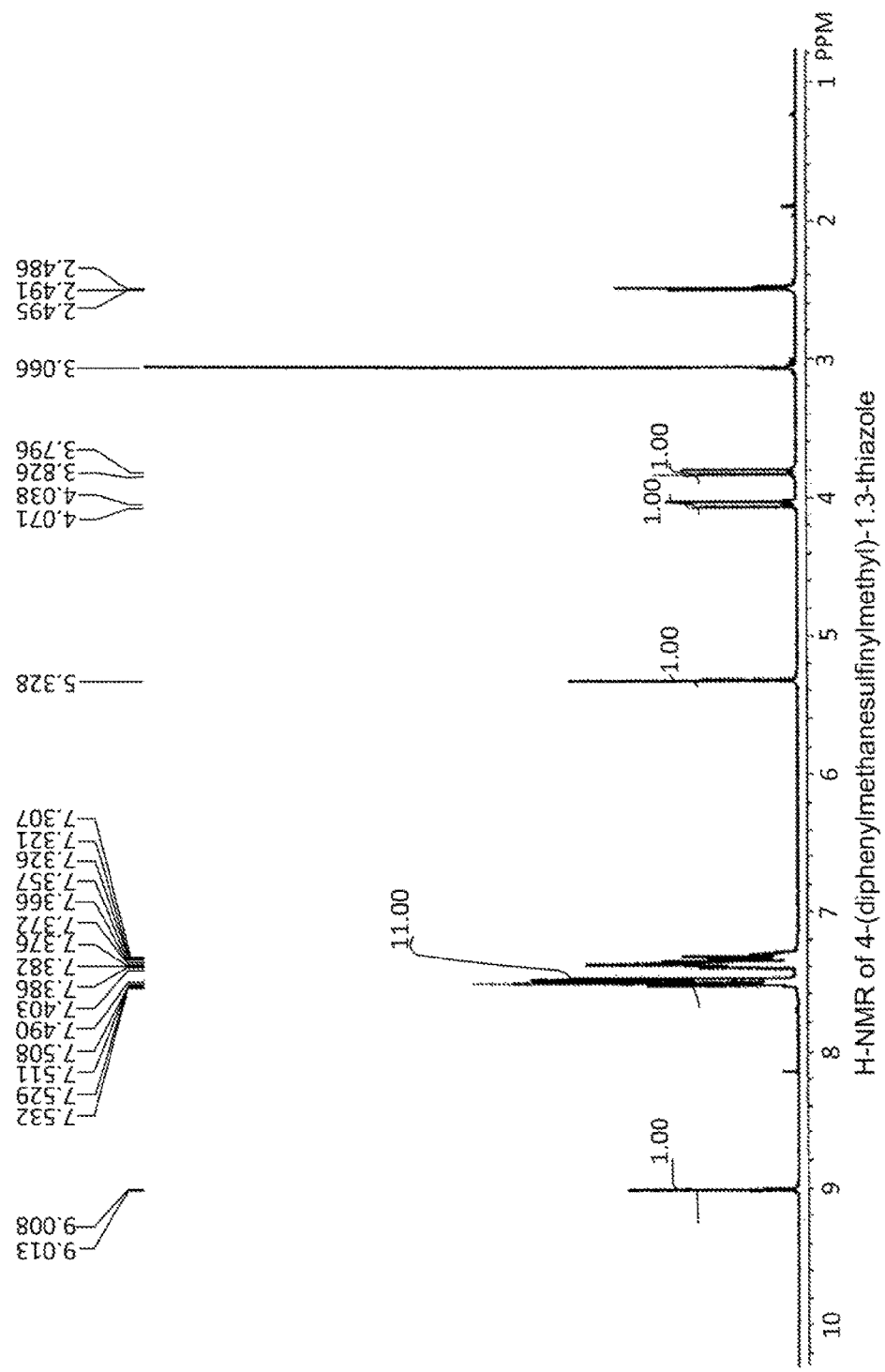
FIG. 3 shows H-NMR of 4-(diphenylmethanesulfinylmethyl)-1,3-thiazole (C2)

The H-NMR of 4-(diphenylmethanesulfinylmethyl)-1,3-thiazole (C2) is shown in FIG. 3.

2. Synthesis of 2-(diphenylmethanesulfinylmethyl}-1,3-thiazole (C1)

2-(Benzhydrylthio)acetic acid

Thioglycolic acid (10.5 g, 7.92 ml (d=1.325), 0.114 mol) was added dropwise to the solution of diphenylmethanol in trifluoroacetic acid (100 ml). The formation of precipitate was observed in 30 min. The reaction mixture was stirred at room temperature for 3 h. The resulting precipitate was filtered off, washed with water (3×50 ml) and hexanes. The crude product was recrystallized from EtOAc/hexanes to get colorless precipitate of 2-(Benzhydrylthio)acetic acid. Yield: 17.93 g (64%). M.p. 121° C.

2-(Benzhydrylthio)acetamide 2-(Benzhydrylthio)acetic acid (12.05 g, 0.0466 mol) was suspended in anhydrous benzene (60 ml) and the solution of $SOCl_2$ (22.197 g, 13.41 ml (d=1.655), 0.186 mol) in benzene (14 ml) was added to the suspension slowly. The mixture was refluxed for 2 h. Then the solvent was evaporated and the resulting oil was re-dissolved in DCM, cooled in an ice-bath and dry $NH_3$ (gas) was bubbled in to the solution during 2 h. The resulting suspension was diluted by $NaHCO_3$ (10% aq. solution) and extracted with DCM. The organic layer was washed with brine and dried over $Na_2SO_4$. Solvent was evaporated and the formed colorless precipitate of 2-(Benzhydrylthio)acetamide was washed with ether. Yield: 69% (8.25 g). M.p. 95-100° C.

2-(Benzhydrylthio)ethanethioamide

The mixture of amide 2-(Benzhydrylthio)acetamide (4 g, 0.0155 mol) and Lawesson's reagent (3.44 g, 0.0085 mol, 0.55 eq.) in anhydrous dioxane (50 ml) was refluxed for 2 h. The solvent was evaporated till dryness. The resulting yellow oil was dissolved in DCM, washed with water and brine. The solution was dried over $Na_2SO_4$. The crude product was purified with flash column chromatography (EtOAc/hexanes 1:2→1:1). Pure 2-(Benzhydrylthio)ethanethioamide was obtained as colorless precipitate (62%, 2.63 g). M.p. 96-99° C.

2-(Benzhydrylthiomethyl)thiazole

The solution of 2-(Benzhydrylthio)ethanethioamide (1.0 g, mol, 1 eq.) and 1,2-dichloro-1-ethoxyethane (0.43 g, 0.37 mL, 0.003 mol, 2 eq.) in 10 mL of anhydrous dimethylformamide (DMF) was heated for 2 h at 90-95° C. and 2 h more at 120-125° C. The solvent was evaporated in vacuum till dryness. The black residue was dissolved in hot ethyl acetate and filtered through silica gel. The filtrate was concentrated in vacuum and the crude product was purified by flash column chromatography (silica gel, EtOAc/hexane=1/6) to yield 2-(benzhydrylthiomethyl)thiazol in 34% as brownish precipitate. M.p. 72-74° C.

2-(diphenylmethanesulfinylmethyl}-1,3-thiazole (C1)

To the solution of 2-(Benzhydrylthiomethyl)thiazole (0.39 g, 0.0013 mol) in glacial HOAc (4 ml) the solution of $H_2O_2$ (27.6%, d=1.105, 0.145 ml) was added. The reaction mixture was stirred during 24 h. The reaction mixture was poured on ice. The formed precipitate was filtered off. The crude product was purified by flash column chromatography (silica gel, EtOAc/hexane=1/1) to yield C1 in 74% as colorless precipitate. M.p. 119-122° C.

NMR (400 MHz, DMSO-$d_6$+$CCl_4$): 3.98 (1H, d, J=14 Hz, $CH_2$), 4.28 (1H, d, J=14 Hz, $CH_2$), 5.38 (1H, s, CH), 7.31-7.42 (6H, m, $H_{arom.}$), 7.47 (2H, d, J=7.2 Hz, $H_{arom.}$), 7.53 (2H, d, J=7.2 Hz, $H_{arom.}$), 7.59 (1H, d, J=3.6 Hz, $H_{thiaz.}$), 7.81 (1H, d, J=3.6 Hz, $CH_{thiaz.}$).

MS: [M+1]=314.06

Figure 4:
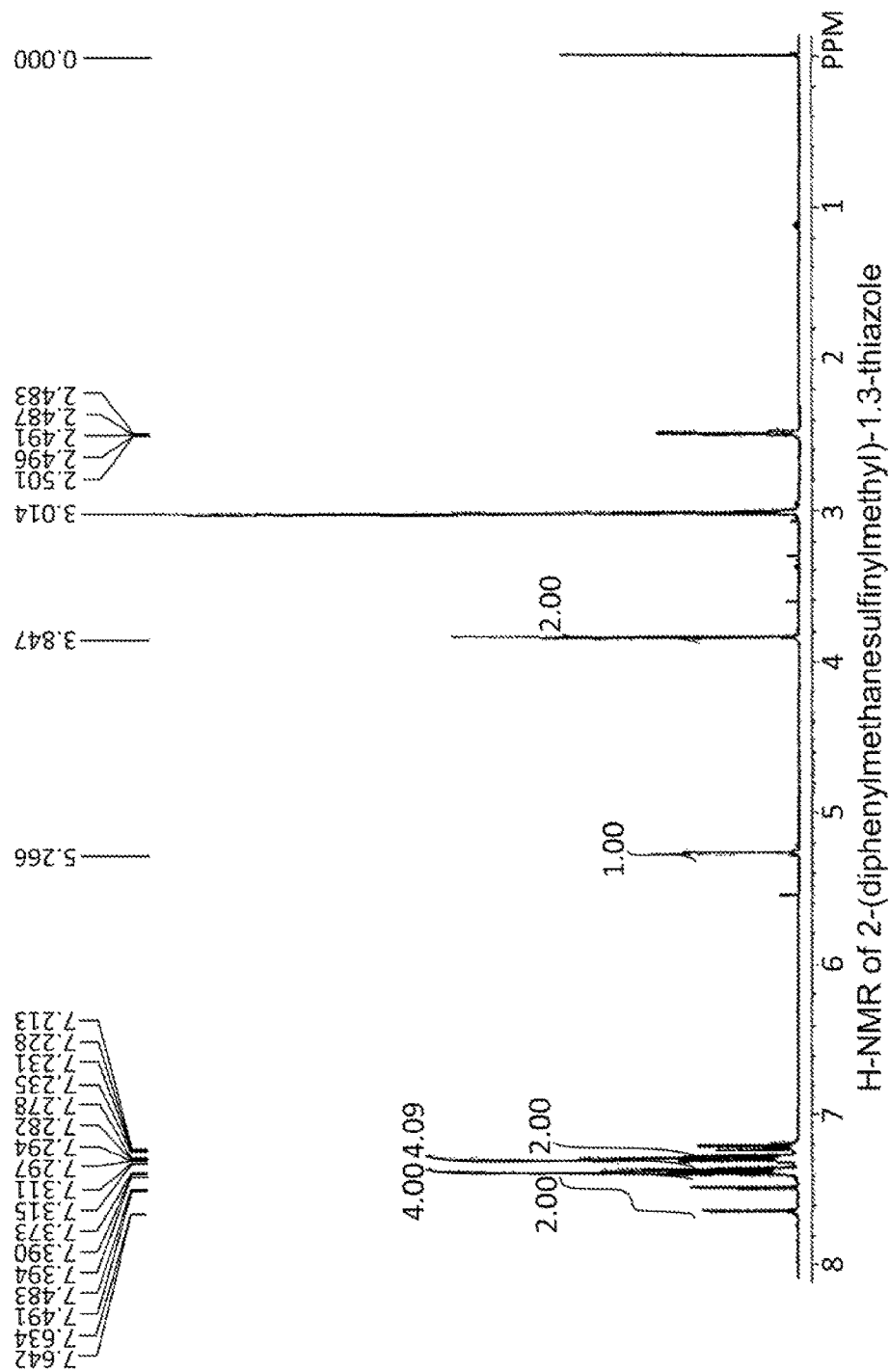
FIG. 4 shows H-NMR of 2-(diphenylmethanesulfinylmethyl}-1,3-thiazole (C1)

NMR of 2-(diphenylmethanesulfinylmethyl}-1,3-thiazole (C1) is shown in FIG. 4.

3. Synthesis of 2-(diphenylmethanesulfinylmethyl)-4-methyl-1,3-thiazole (C3)

2-(Benzhydrylthiomethyl)-4-methylthiazole

α-Chloroacetone (0.41 ml, 0.00512 mol, 1.4 eq) was added to the solution of 2-(Benzhydrylthio)acetamide (1 g, 0.00366 mol, 1.0 eq.) in dry EtOH (16 ml) and the resulting mixture was refluxed during 7 h. The solvent was evaporated till dryness and small amount of EtOAc was added to the resulting oil. The oil was immediately transformed to colorless precipitate. The precipitate was filtered off and washed with EtOAc to obtained 4-methylthiazole in 76% yield (0.866 g). M.p. 154° C.

2-(diphenylmethanesulfinylmethyl)-4-methyl-1,3-thiazole (C3)

To the solution of 4-methylthiazole (0.86 g, 0.00276 mol) in glacial HOAc (16 ml) the solution of $H_2O_2$ (27.6%, d=1.105, 0.31 ml) was added. The reaction mixture was stirred at 30-35° C. during 5 h. The reaction mixture was poured on ice, the resulting oil was extracted with EtOAc, washed with water. The organic layer was dried, evaporated till dryness. The resulting oil was coat with ether and the colorless precipitate was formed at low temperature. Crud product was recrystallized from EtOAc. Yield 61% (0.553 g), m.p. 104-107° C.

NMR $^1$H ($CDCl_3$, 400 MHz): 3.48 (s, 3H, $CH_3$), 3.97 (d, 1H, J=13.6 Hz, $CH_2$), 4.18 (d, 1H, J=13.6 Hz, $CH_2$), 5.13 (s, 1H, CH), (6.89 (s, 1H, $CH_{thiazol.}$), 7.32-7.42 (m, 6H, $H_{arom.}$), 7.48-7.50 (m, 4H, $H_{arom.}$).

MS: [M+1]=328.08

Figure 5:
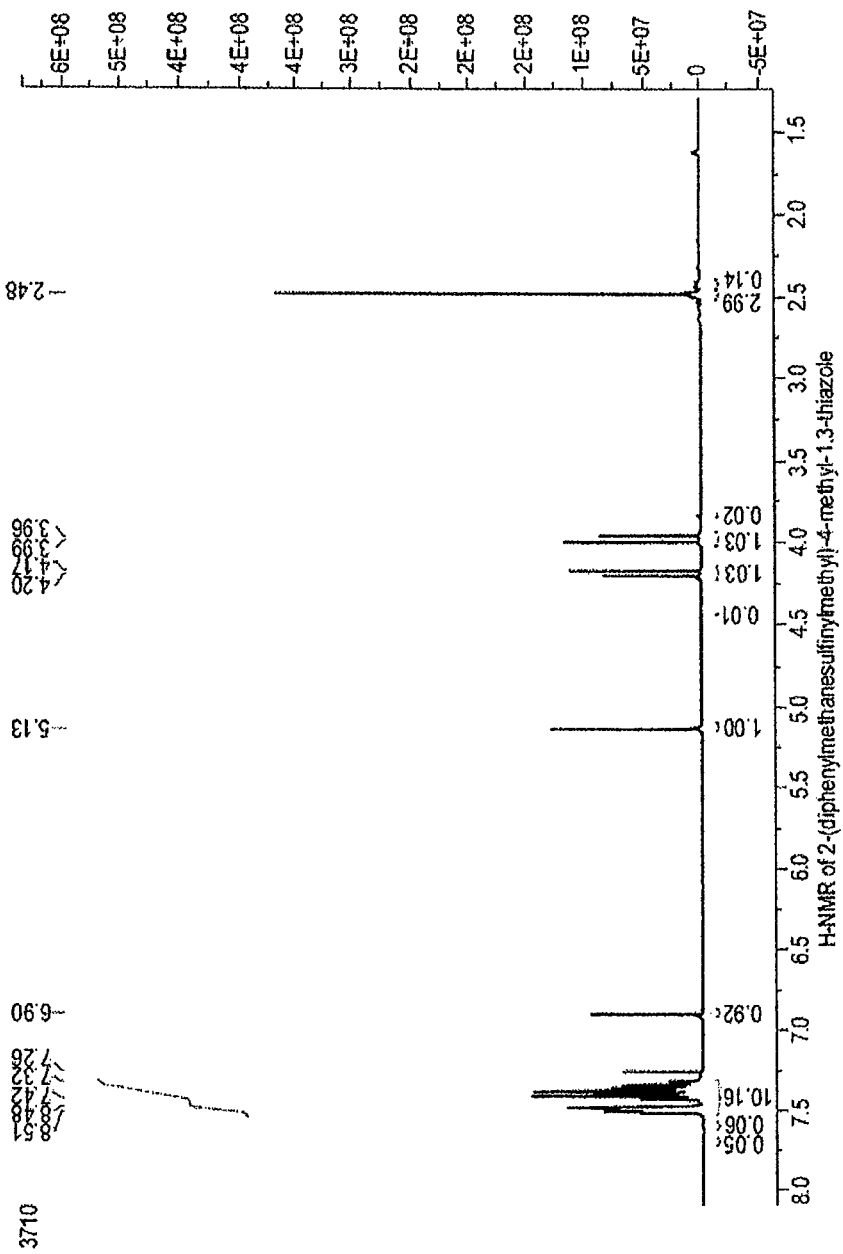
FIG. 5 shows H-NMR of 2-(diphenylmethanesulfinylmethyl)-4-methyl-1,3-thiazole (C3)

The NMR of 2-(diphenylmethanesulfinylmethyl)-4-methyl-1,3-thiazole (C3) is shown in FIG. 5.

4. Synthesis of 4-(Diphenyl-methanesulfinylmethyl)-2-methyl-1,3-thiazole

4-Chloromethyl-2-methyl-thiazole hydrochloride

4-Chloromethyl-2-methyl-thiazole hydrochloride was obtained from Acros Organics (New Jersey, USA; Geel, Belgium). The compound can also be prepared according to literature procedures (Journal of Organic Chemistry, 1979, Volume 44, Issue 4, p. 497-501).

[(Diphenylmethyl)sulfanyl]methanimideamide

Diphenylmethanol (13 g, 0.07 mol) and thiourea (6.5 g, 0.085 mol) are added in 0.5 L flask and 32.5 ml of water was added. The mixture was then heated to 95° C. (an emulsion was obtained) and 26 g of 48% HBr (0.322 mol, 4.6 equivalents) was then gradually added during 0.5 h. The mixture was heated under reflux (106-107° C.) for 0.5 h and cooled to 80-85° C. The mixture was then cooled in ice and precipitate with crystals is formed. After filtration and washing with water colorless crystalline substance is obtained. The product was then dried in the high vacuum. 9.62 g of the product was obtained as a white crystalline solid (yield: 74%).

4-Benzhydrylsylfanylmethyl-2-methyl-thiazole

In a round bottom flask 3.51 g (10.86 mmol) of [(diphenylmethyl)sulfanyl]methanimideamide was dissolved in 75 ml of methanol. Afterwards, 2 g (10.86 mmol) of 4-chloromethyl-2-methyl-1,3-thiazole and 7.5 g (5 equivalents) of potassium carbonate were added to the mixture. The mixture was left to stir overnight at room temperature.

Methanol was evaporated and water was added. Then solution was extracted (3×) with 100 ml of ethylacetate. Organic phases were collected, combined, dried with $Na_2SO_4$, filtered. Ethylacetate was removed by rotary evaporation. Semi-solid product was obtained. Crude product was purified via flash column chromatography on silica gel. 5% methanol in dichloromethane was used as mobile phase. 2.6 g of the crude solid product was obtained (yield: 59.07%).

NMR (200 MHz, DMSO-$d_6$): 2.63 (3H, s, $CH_3$), 3.62 (2H, s, $CH_2$), 5.33 (1H, s, CH), 7.15 (1H, s, $CH_{thiazole}$), 7.21-7.46 (10H, m, $CH_{aromatic}$).

Synthesis of 4-(Diphenyl-methanesulfinylmethyl)-2-methyl-1,3-thiazole

In a round bottom flask, 1.44 g (4.62 mmol) of 4-Benzhydrylsylfanylmethyl-2-methyl-thiazole was dissolved in 10 ml of glacial acetic acid (174.82 mmol). 0.55 ml (4.85 mmol) was dropped into the solution and stirred for 12 hrs.

Acid was neutralized with 5% sodium bicarbonate and ice. Aqueous mixture was extracted (3×) with 50 ml of ethyl acetate. Organic phases were collected, combined, dried with $Na_2SO_4$, filtered and ethyl acetate was concentrated on rotary evaporator.

Semi solid product was purified via flash column chromatography on silica gel. 5% methanol in dichloromethane was used as a mobile phase. Product was dried in a high vacuum. By this procedure 1.12 g of the final pure product was obtained (yield: 73.98%).

MS. [M+H$^+$]=328.00 (MW is 327.46), [M+Na+]=350.13.

NMR (200 MHz, DMSO-$d_6$): 2.65 (3H, s, $CH_3$), 3.73-3.99 (2H, dd, $CH_2$), 5.43 (1H, s, CH), 7.32-7.58 (11H, aromatic CH).

Figure 2:
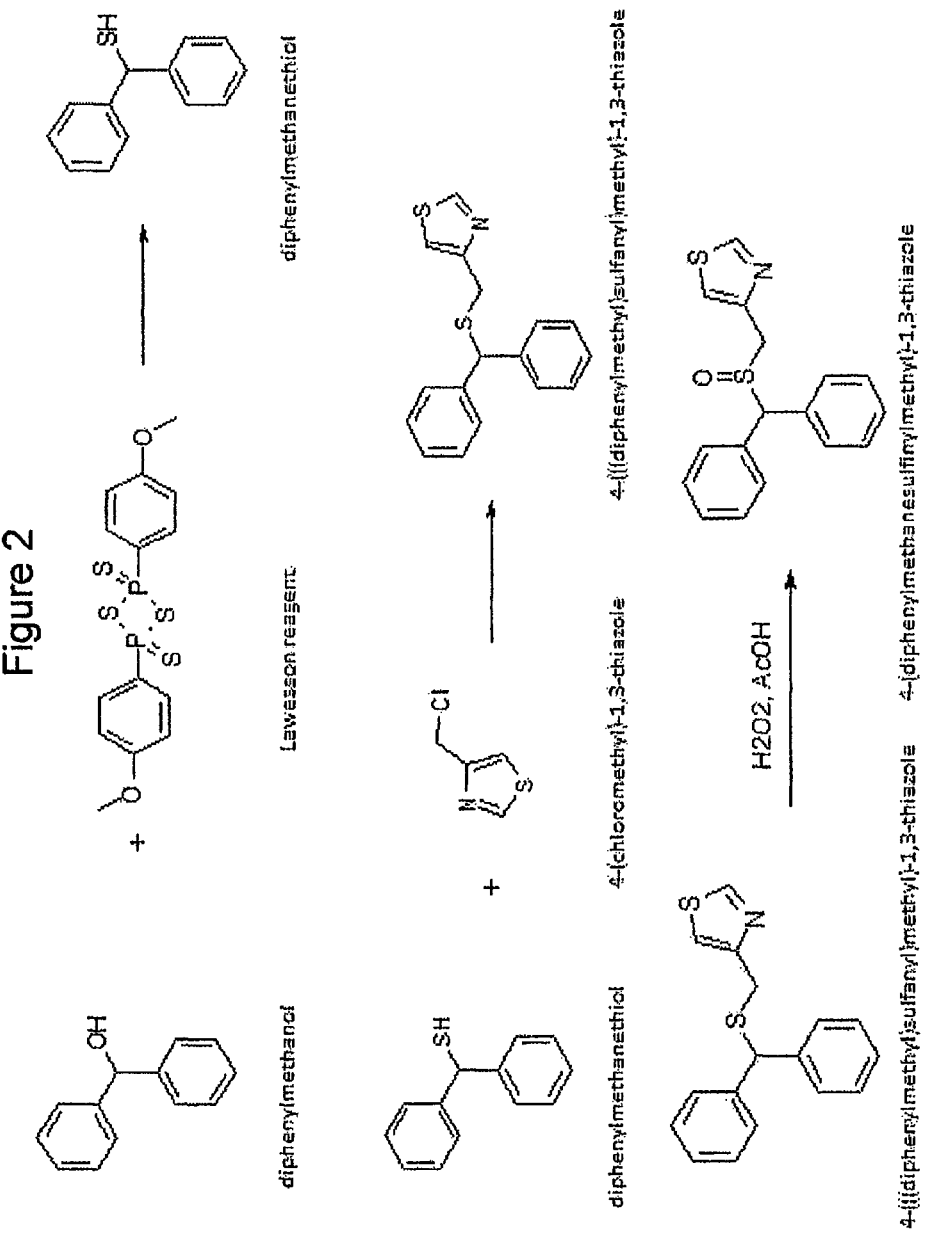
FIG. 2 shows scheme (2) for the synthesis of compounds as exemplified by 4-(diphenylmethanesulfinylmethyl)-1,3-thiazole (C2)

It is evident that the compounds according to the present disclosure can be provided by applying the above methods. For example, the compounds according to FIG. 5 can be prepared accordingly. In FIGS. 1 and 2, such methods are exemplified by the two compounds produced above.

B. Experiments Demonstrating Cognitive Enhancing Effects

The compound of the present disclosure can be used for cognitive enhancement of working memory of normal and aged individuals with and without a variety of human diseases, where inhibition of the improvement of working memory is beneficial.

The compounds of the present disclosure were demonstrated to have cognitive enhancing activity and more specifically working memory enhancing activity in an animal model. One such animal model is the radial arm maze using rats and is given in detail in Timofeva O. et al., Brain Res. 1308 (2010) 147-152: Wenk G. et al.; The Journal of Neuroscience (2004) 8.5A.1-8.5A.12; Akoto M. et al.; The Journal of Neuroscience (2000)20 (189: 7116-7121: Levin E D et al.; Behavioral Brain Res. 208 (2010) 319-327. Li-Bo Z. et al.; Neuropharmacology 37, 1998) 323-330. Roegge, C S. et al.; Toxicological Sciences 57, 121-30 (2000).

Male Sprague Dawley rats were used for the studies aged between 12-14 weeks. Twelve rats per group were used for this study. All rats were obtained from Core Unit of Biomedical Research, Division of Laboratory Animal Science and Genetics, Medical University of Vienna and maintained in cages made of makrolon and filled with autoclaved woodchips and water in bottles was available ad libitum. The room was illuminated with artificial light at an intensity of about 200 lx in 2 m from 5 am to 7 pm. Radial arm maze (RAM) training was performed between 8:00 h and 13:00 h.

All procedures were carried out according to the guidelines of the Ethics committee, Medical University of Vienna, and were approved by the Federal Ministry of Education, Science and Culture, Austria (BMWF-). All efforts were made to minimize animal suffering and to reduce the number of animals used.

Radial Arm Maze:

Rats were trained in the 12 arm radial maze. Rats were handled for 5 days for adaptation (30 min/day/rat) and also to reduce the body weight to 85%. Water was provided ad libitum during the training. The amount of food was provided to maintain a lean, healthy body weight of approximately 85% of the free-feeding weight during the training.

The maze is made out of black plastic and kept at an elevation of 80 cm above the floor in a room with numerous visual cues. The central platform has a diameter of 50 cm and 12 arms (12 cm×60 cm) are projecting radially outwards. A plastic cylinder is used to restrict the movements of rats in the center before being released to the start of training. The lifting of the cylinder is controlled by a pulley system from the far end of the room. Out of 12 arms, 8 arms were baited with food during the training and 4 arms remained un-baited. Food reward was placed in the baited arms 1 cm from the distal end.

Compound Dosing

Before starting the training, rats were given two habituation sessions in which food was placed all over the maze and rats were allowed to explore the maze and consume the food for 5 minutes. During the training session, the same arms were baited for each rat once at the beginning of each session to assess working memory, while the other four arms were always left un-baited to test reference memory. The pattern of baited and un-baited arms was consistent throughout testing for each rat but differed among rats. Each trial began by placing the rat in the central platform, after 10 seconds the cylinder was lifted slowly and rats were allowed to enter any arm. The session lasted 8 minutes or until all 8 baited arms were entered. An arm was baited only once and a repeated entry into a baited arm was counted as a working memory error, whereas any entry into an un-baited arm was recorded as a reference memory error. The rats were given 10 training sessions over a period of 10 days.

The overall analysis of working and reference memory errors over the 10 sessions of acquisition was then carried out using ANOVA statistics

C. Results

Figure 6:
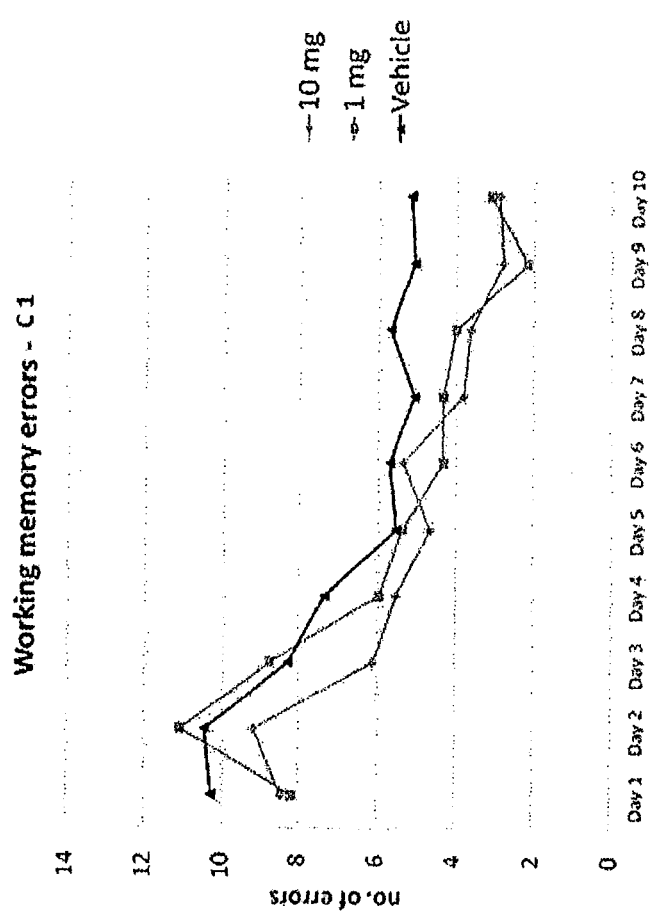
FIG. 6 shows results of the administration of the compound C1 according to the present disclosure in an accepted animal model and FIG. 7 shows the assessment of FIG. 6 including standard deviation.

The results are depicted in FIG. 6. It can be seen that with the compound according to the present disclosure, a significant reduction in memory errors can be achieved, both, with the 1 mg and the 10 mg dose.

Figure 7:
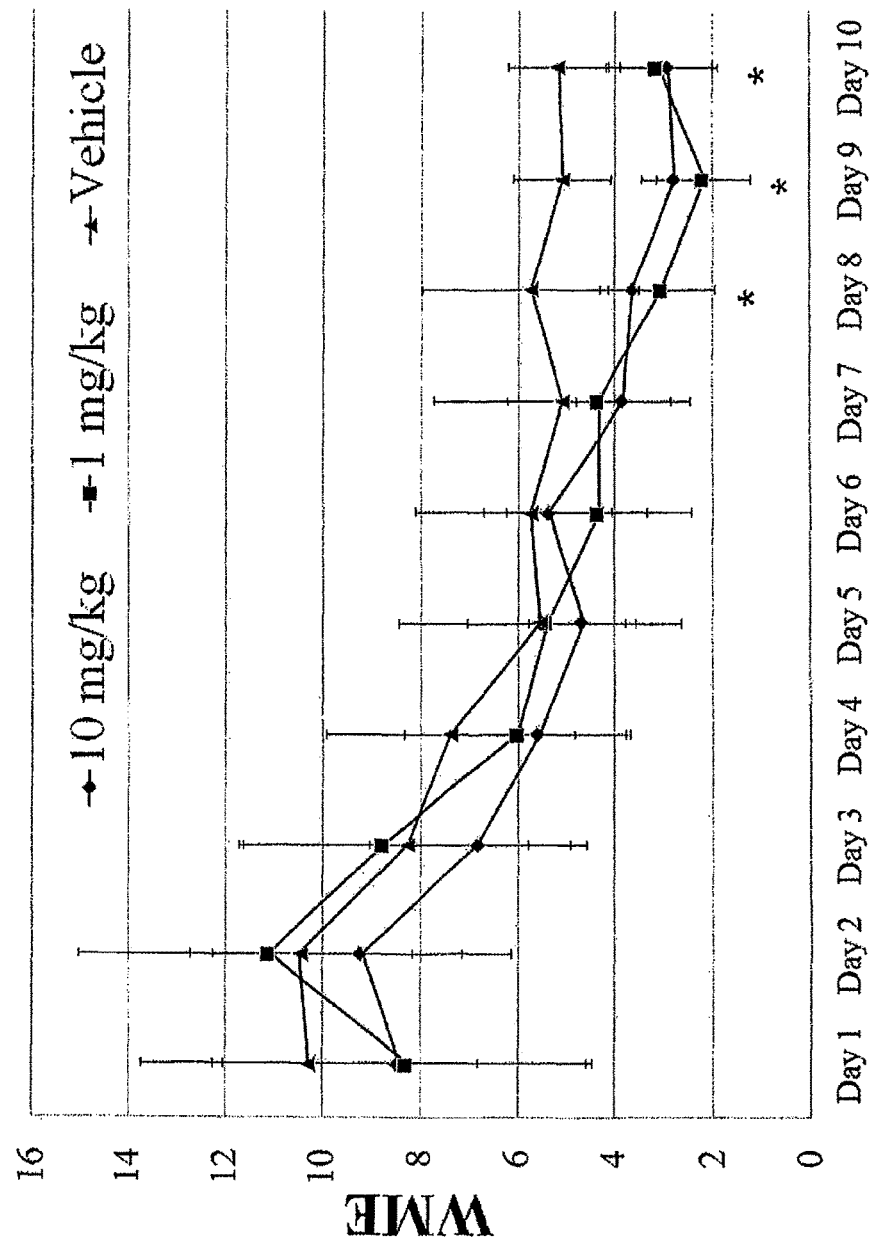

Rats that received C1 performed at a comparable level in the RAM training up to day seven, but from day eight TDI animals performed better as compared with their counterparts injected with DMSO. Data analyzed used ANOVA and Bonferrini post hoc test. Trained rats showed decrease in working memory errors as days progressed (F (9, 750)=83.51; P<0.0001). TDI rats continued to decrease working memory errors significantly from day eight to ten (F (6, 750)=7.630; P<0.0001). * p<0.05; n=10-12 per group. Data is represented as mean±SD in FIG. 7.

D. Synthesis of 4-(diphenylmethanesulfinylmethyl)-2-cyclopropyl-1,3-thiazole The compound was synthesized as follows:

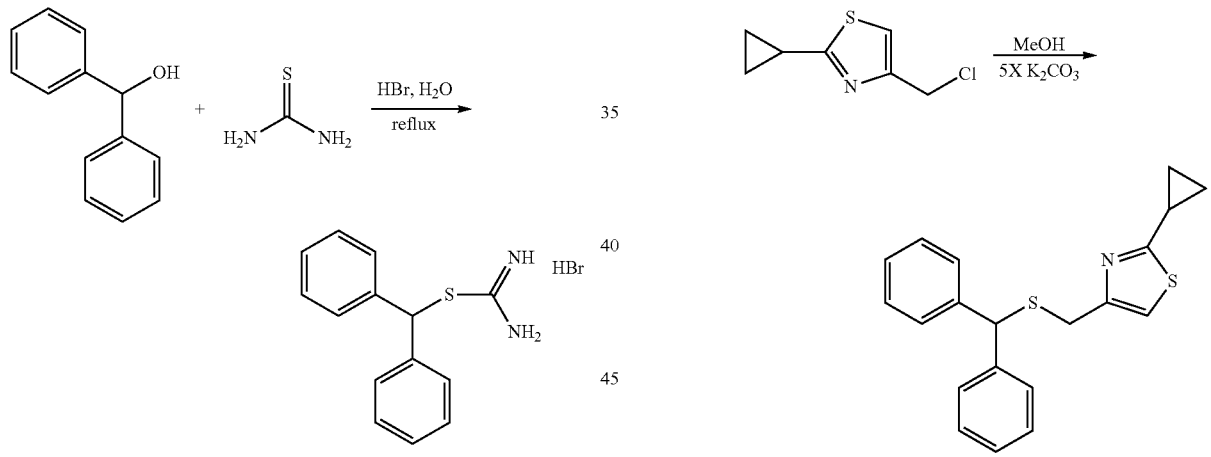

Diphenylmethanol (13 g, 0.07 mol) and thiourea (6.5 g, 0.085 mol) were added in 0.5 L flask and 32.5 ml of water was added. The mixture was heated to 95° C. (an emulsion was obtained) and 26 g of 48% HBr (0.322 mol, 4.6 equivalents) was then gradually added during 0.5 h. The mixture was heated under reflux (106-107° C.) for 0.5 h and cooled to 80-85° C. The mixture was cooled in ice and precipitate with crystals was formed. After filtration and washing with water colorless crystalline substance was obtained. The product was then dried in the high vacuum. 9.62 g of the product was obtained as a white crystalline solid (yield: 74%).

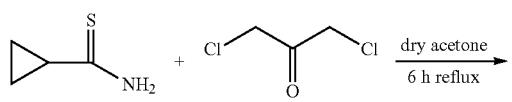

-continued

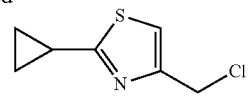

In a round bottom flask, 0.5 g (5 mmol) of cyclopropanecarbothioamide was dissolved in 10-15 ml of dry acetone and then 0.6 g (5 mmol) of 1,3-dichloropropan-2-one was added. Reaction mixture was stirred under total reflux for 6 h and left to cool afterwards overnight at the room temperature. Solvent was evaporated on rotary vapor and the product was dried on a high vacuum pump equipped with a cold trap. Crude gummy product was then used for further synthesis as such.

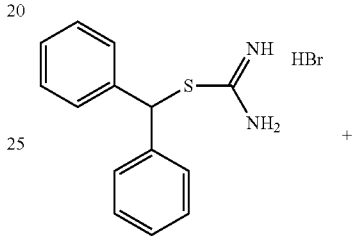

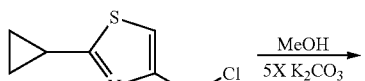

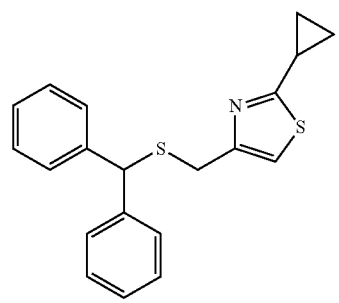

In a round bottom flask 0.95 g (2.9 mmol) of [(diphenylmethyl)sulfanyl]methanimideamide was dissolved in 50 ml of methanol. Afterwards, 0.5 g (2.9 mmol) of 4-(chloromethyl)-2-cyclopropylthiazole and 2.02 g (5 equivalents) of potassium carbonate were added to the mixture. The mixture was left to stir for 2 days at room temperature. Methanol was evaporated and water was added. Then solution was extracted (3×) with 100 ml of ethylacetate. Organic phases were collected, combined, dried with Na$_2$SO$_4$, filtered. Ethylacetate was removed by rotary evaporation. Crude product was purified via flash column chromatography on silica gel. 5% methanol in dichloromethane was used as mobile phase. Product was concentrated via rotary vapor and cooled in refrigerator overnight. Gum-like product is obtained and used directly for the next reaction.

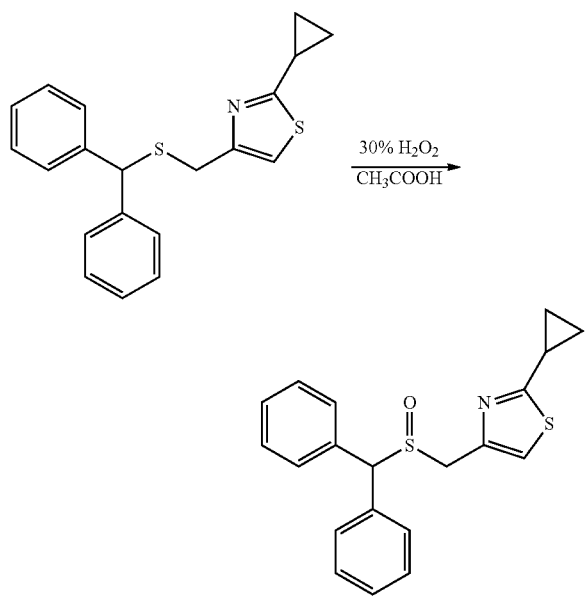

In a round bottom flask, 0.6 g (1.59 mmol) of 4-((benzhydrylthio)methyl)-2-cyclopropylthiazole was dissolved in 10 ml of glacial acetic acid. 0.46 ml (4.05 mmol) hydrogen peroxide was dropped into the solution and stirred for 12 hrs. Acid was neutralized with 5% sodium bicarbonate in ice. Aqueous mixture was extracted (3×) with 50 ml of ethyl acetate. Organic phases were collected, combined, dried with $Na_2SO_4$, filtered and ethyl acetate is concentrated on rotary evaporator. Solid product was purified via flash column chromatography on silica gel. 5% methanol in dichloromethane was used as a mobile phase. Compound was afterwards dried in a high vacuum and left in refrigerator overnight. By this procedure 0.3 g of the solid white material was obtained (yield: 53.44%)

[M+H+]=354.00, [M+Na+]=376.00

NMR (200 MHz, DMSO-d6): 1.23 (4H, s, aliphatic), 2.42 (1H, s, aliphatic), 3.81-4.10 (2H, dd, aliphatic), 5.23 (1H, s, aliphatic), 7.11-7.62 (11H, m, aromatic).

E. Experiments Demonstrating Inhibition of the Dopamine Transporter (DAT)

4-(diphenylmethanesulfinylmethyl)-2-cyclopropyl-1,3-thiazole and 4-diphenylmethanesulfinylmethyl)-1,3-thiazole have been tested according to the following method.

The human isoforms of DAT, SERT and NET were expressed in HEK293 (HEK-DAT, HEK-SERT and HEK-NET) cells. DAT inhibitors-mediated monoamine transporter effects on substrate uptake were analyzed according to procedure described by Sitte et al. In brief, cells were grown in poly-d-lysine coated 96-well plates, incubated with compounds diluted in Krebs-Ringer-HEPES buffer, substrates were subsequently added, cells were lysed with 1% SDS (sodium dodecyl sulphate) and released radioactivity was measure by a liquid scintillation counter (23).

$EC_{50}$-values for the dopamine transporter (DAT), the norepinephrine transporter (NET) and the serotonin transporter (SERT) were obtained:

| 4-(diphenylmethanesulfinyl-methyl)-2-cyclopropyl-1,3-thiazole | 4-(diphenylmethanesulfinylmethyl)-1,3-thiazole |
|---|---|
| $EC_{50}(DAT) = 4.1\ \mu M$ | $EC_{50}(DAT) = 7.3\ \mu M$ |
| $EC_{50}(SERT) = 436.1\ \mu M$ | $EC_{50}(SERT) = 455.5\ \mu M$ |
| $EC_{50}(NET) = 774.3\ \mu M$ | $EC_{50}(NET) = 547.0\ \mu M$ |

Thus excellent inhibition and selectivity against SERT and NET was found for the DAT-Inhibitors 4-(diphenylmethanesulfinylmethyl)-2-cyclopropyl-1,3-thiazole and 4-(diphenylmethanesulfinylmethyl)-1,3-thiazole.

Although modifications and changes maybe suggested by those skilled in the art, it is the intention of the applicant to embody within the patent warranted hereon all changes and modifications as reasonably and probably come within the scope of this contribution to the art. The features of the present disclosure which are believed to be novel are set forth in detail in the appended claims. The features disclosed in the description, the figures as well as the claims could be essential alone or in every combination for the realization of the present disclosure in its different embodiments.

The invention claimed is:

1. Chemical compound having the general formula (I):

formula (I)

wherein $R_1$ and $R_2$ are, equal or independently, aryl or substituted aryl;

$R_{TA}$ is a 2-1,3-, or 4-1,3- or 5-1,3-thiazole ring with the general Formula (IIa):

Formula (IIa)

$R_3$ is present on the ring according to Formula (IIa), 1 or 2 times, equal or independently, wherein $R_3$ is selected from the group consisting of hydrogen, alkyl, cycloalkyl, heterocycloalkyl, halo, and alkoxy.

2. Compound according to claim 1, wherein
$R_{TA}$ is a 4-thiazole group, 2-thiazole, and 2-methyl-4-thiazole.

3. Compound according to claim 1, wherein
alkyl is selected from the group consisting of methyl, ethyl, n-propyl, iso-propyl and tert-butyl, or wherein hydroxyalkyl is hydroxymethyl.

4. Compound according to claim 1, wherein
$R_3$ is hydrogen or alkyl or oxyalkyl.

5. Compound according to claim 1, wherein
it is selected from the group consisting of
2-(diphenylmethanesulfinylmethyl)-1,3-thiazole,
4-(diphenylmethanesulfinylmethyl)-1,3-thiazole,
2-(diphenylmethanesulfinylmethyl)-4-methyl-1,3-thiazole, and
4-(diphenylmethanesulfinylmethyl)-2-methyl-1,3-thiazole.

6. Compound according to claim 5, wherein
it is 4-(diphenylmethanesulfinylmethyl)-2-methyl-1,3-thiazole.

7. Compound according to claim 1, wherein
$R_1$ and $R_2$ are, equal or independently, aryl or substituted aryl,
wherein $R_3$ is present on $R_{T4}$ according to Formula (IIa) 2 times and selected from the group consisting of $R_4$, $R_5$, $R_6$ and $R_7$,
wherein $R_{T4}$ is a 4-1,3-thiazole ring with the general Formula (Ma)

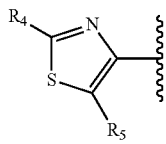

Formula (IIIa)

wherein $R_4$ is selected from the group consisting of oxirane, cyclopropyl, cyclobutyl, cyclopentyl and cyclohexyl and
wherein $R_5$ is selected from the group consisting of hydrogen, methyl, n-propyl, iso-propyl,
or
wherein $R_{T4}$ is a 5-1,3-thiazole ring with the general Formula (IIIb)

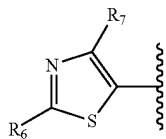

Formula (IIIb)

wherein $R_6$ is selected from the group consisting of hydrogen, methyl, n-propyl, iso-propyl, cyclopropyl, cyclobutyl, cyclopentyl and cyclohexyl, and
wherein $R_7$ is selected from the group consisting of hydrogen, methyl, n-propyl, iso-propyl, cyclopropyl, cyclobutyl, cyclopentyl and cyclohexyl.

8. Compound according to claim 4, wherein
$R_3$ is methyl or oxymethyl.

9. Compound according to claim 1,
wherein $R_1$ and $R_2$ are, equal or independently, aryl or substituted aryl,
wherein $R_{T4}$ is a 4-1,3-thiazole ring with the general Formula (Ma)

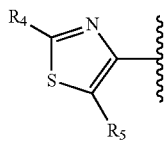

Formula (IIIa)

wherein $R_4$ is selected from the group consisting of oxirane, cyclopropyl, cyclobutyl, cyclopentyl and cyclohexyl and wherein $R_5$ is selected from the group consisting of hydrogen, methyl, n-propyl, iso-propyl, fluoro, chloro, bromo and iodo,
or
wherein $R_{T4}$ is a 5-1,3-thiazole ring with the general Formula (Mb)

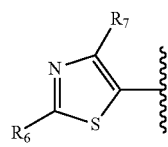

Formula (IIIb)

wherein $R_6$ is selected from the group consisting of hydrogen, methyl, n-propyl, iso-propyl, fluoro, chloro, bromo, iodo, cyclopropyl, cyclobutyl, cyclopentyl and cyclohexyl, and
wherein $R_7$ is selected from the group consisting of hydrogen, methyl, n-propyl, iso-propyl, fluoro, chloro, bromo, iodo, cyclopropyl, cyclobutyl, cyclopentyl and cyclohexyl.

10. Compound according to claim 9, wherein
both of $R_1$ and $R_2$ are phenyl.

11. Compound according to claim 9, wherein
$R_4$ is cyclopropyl and wherein $R_5$ is hydrogen.

12. Compound according to claim 9, wherein
both $R_6$ and $R_7$ are hydrogen.

13. Compound according to claim 9, wherein
it is selected from the group consisting of
5-(diphenylmethanesulfinylmethyl)-1,3-thiazole,
5-(diphenylmethanesulfinylmethyl)-2-chloro-1,3-thiazole,
5-(diphenylmethanesulfinylmethyl)-2-methyl-1,3-thiazole,
5-(diphenylmethanesulfinylmethyl)-4-methyl-1,3-thiazole,
5-(diphenylmethanesulfinylmethyl)-4-chloro-1,3-thiazole,
5-(diphenylmethanesulfinylmethyl)-2-methyl-4-methyl-1,3-thiazole,
5-(diphenylmethanesulfinylmethyl)-2-methyl-4-chloro-1,3-thiazole,
5-(diphenylmethanesulfinylmethyl)-2-chloro-4-methyl-1,3-thiazole,
5-(diphenylmethanesulfinylmethyl)-2-cyclopropyl-1,3-thiazole,
4-(diphenylmethanesulfinylmethyl)-2-oxirane-1,3-thiazole,
4-(diphenylmethanesulfinylmethyl)-2-cyclopropyl-5-methyl-1,3-thiazole,
4-(diphenylmethanesulfinylmethyl)-2-cyclopropyl-5-chloro-1,3-thiazole, and
4-(diphenylmethanesulfinylmethyl)-2-cyclopropyl-1,3-thiazole.

14. Compound according to claim 9, wherein
it is 4-(diphenylmethanesulfinylmethyl)-2-cyclopropyl-1,3-thiazole or 5-(diphenylmethanesulfinylmethyl)-1,3-thiazole.

* * * * *